US005395929A

United States Patent [19]
Corbi et al.

[11] Patent Number: 5,395,929
[45] Date of Patent: Mar. 7, 1995

[54] ISOLATED NUCLEIC ACID ENCODING THE ALPHA SUBUNIT OF THE HUMAN LEUKOCYTE ADHESION RECEPTOR

[75] Inventors: Angel A. Corbi, Madrid, Spain; Timothy A. Springer, Newton, Mass.

[73] Assignee: Dana Farber Cancer Institute, Boston, Mass.

[21] Appl. No.: 67,969

[22] Filed: May 27, 1993

Related U.S. Application Data

[63] Continuation of Ser. No. 920,533, Jul. 28, 1992, abandoned, which is a continuation of Ser. No. 321,018, Mar. 9, 1989, abandoned, which is a continuation-in-part of Ser. No. 133,399, Dec. 15, 1987, abandoned.

[51] Int. Cl.$^6$ ............... C07H 17/00; C12N 15/00; A61K 37/00; C07K 13/00
[52] U.S. Cl. ............... 536/23.5; 536/23.51; 435/320.1; 530/399
[58] Field of Search ............... 536/23.5, 23.51; 435/320.1; 514/12; 530/399

[56] References Cited

U.S. PATENT DOCUMENTS

4,761,371 8/1988 Bell et al. ............... 435/68
4,935,234 6/1990 Todd, III et al. ............... 424/85.8
4,956,281 9/1990 Wallner et al. ............... 435/69.3

FOREIGN PATENT DOCUMENTS

0362526 4/1990 European Pat. Off. .
0364690 4/1990 European Pat. Off. .
WO90/13316 11/1990 WIPO .

OTHER PUBLICATIONS

Anderson et al. Jul. 1986, J. Immunol. 137:15–27.
Lathe, 1985, J. Mol. Biol. 183:1–12.
Miller et al. Apr. 1987, J. Immunol. 138:2381–2383.
Yang et al. Oct. 1986, Cell 47:3–10.
Young et al. 1983, PNAS USA 80:1194–1198.
Anderson, D. C. et al., Abnormalities of Polymorphonuclear Leukocyte Function Associated with a Heritable Deficiency of High Molecular Weight Surface Glycoproteins (GP 138): Common Relationship to Diminished Cell Adherence, *J. Clin. Invest.* 74:536–551 (Aug. 1984).
Anderson, D. C. et al., Contributions of The Mac–1 Glycoprotein Family to Adherence–Dependent Granulocyte Functions: Structure–Function Assessments Employing Subunit–Specific Monoclonal Antibodies, *J. Immunol.* 137(1):15–27 (Jul. 1, 1986).
Anderson, D. C. et al., The Severe and Moderate Phenotypes of Heritable Mac–1, LFA–1 Deficiency: Their Quantitative Definition and Relation to Leukocyte Dysfunction and Clinical Features, *J. Inf. Dis.* 152(4):668–689 (Oct. 1985).
Beller, D. I. et al., Anti–Mac–1 Selectively Inhibits the Mouse and Human Type Three Complement Receptor, *J. Exp. Med.* 156:1000–1009 (Oct. 1982).
Brian, A. A. et al., Allogeneic stimulation of cytotoxic T cells by supported planar membranes, *Proc. Natl. Acad. Sci. USA* 81:6159–6163 (Oct. 1984).
Bullock, W. E. et al., Role of the Adherence–Promoting Receptors, CR3, LFA–1, and p150,95, In Binding of *Histoplama capsulatum* by Human Macrophages, *J. Exp. Med.* 165:195–210 (Jan. 1987).

(List continued on next page.)

*Primary Examiner*—Garnette D. Draper
*Assistant Examiner*—Elizabeth C. Kemmerer
*Attorney, Agent, or Firm*—Stern, Kessler, Goldstein & Fox

[57] ABSTRACT

This invention concerns the cloning of the alpha-subunit of the p150,95 leukocyte adhesion receptor molecule. The invention also concerns the alpha-subunit of p150,95, as well as fragments of this receptor molecule. The invention further pertains to the diagnostic and therapeutic uses for such molecules.

6 Claims, 16 Drawing Sheets

OTHER PUBLICATIONS

Cerf-Bensussan, N. et al., Immunohistologic and Immunoelectron Microscopic Characterization of the Mucosal Lymphocytes of Human Small Intestine by the Use of Monoclonal Antibodies, *J. Immunol.* 130(6):2615–2622 (Jun. 1983).

Corbi, A. et al., cDNA Cloning and Primary Sequence of the Alpha Subunit of p150,95, *J. Cell. Biochem.* Suppl. 11D, p. 268, Abstract No. T404 (1987).

Corbi, A. L. et al., cDNA cloning and complete primary structure of the α subunit of a leukocyte adhesion glycoprotein p150,95, *EMBO J.* 6(13):4023–4028 (1987).

Cunningham, B. A. et al., Neural Cell Adhesion Molecule: Structure, Immunoglobulin-Like Domains, Cell Surface Modulation, and Alternative RNA Splicing, *Science* 236:799–806 (May 15, 1987).

Dana, N. et al., Two Functional Domains in the Phagocyte Membrane Glycoprotein Mo1 Identified with Monoclonal Antibodies, *J. Immunol.* 137(10):3259–3263 (Nov. 15, 1986).

Davingnon, D. et al., Lymphocyte function–associated antigen 1 (LFA-1): A surface antigen distinct from Lyt-2, 3 that participates in T lymphocyte-mediated killing, *Proc. Natl. Acad. Sci. USA* 78(7):4535–4539 (Jul. 1981).

Detmers, P. A. et al., Aggregation of Complement Receptors on Human Neutrophils in the Absence of Ligand, *J. Cell Biol.* 105:1137–1145 (1987).

Dustin, M. L., et al., Induction by IL 1 and Interferon-γ: Tissue Distribution, Biochemistry and Function of a Natural Adherence Molecule (ICAM-1), *J. Immunol.* 137(1):245–254 (Jul. 1, 1986).

Dustin, M. L. et al., Purified Lymphocyte Function–Associated Antigen 3 Binds to CD2 and Mediates T Lymphocytes Adhesion, *J. Exp. Med.* 165:677–692 (Mar. 1987).

Fischer, A. et al., Prevention of Graft Failure by an Anti-HLFA-1 Monoclonal Antibody in HLA-Mismatched Bone-Marrow Transplatation, *Lancet*:1058–1061 (Nov. 8, 1986).

Fischer, A. et al., Role of the LFA-1 Molecular in Cellular Interactions Required for Antibody Production in Humans, *J. Immunol.* 136(9):3198–3203 (May 1, 1986).

Gay, D. et al., The Major Histocompatibility Complex-Restricted Antigen Receptor on T Cells, *J. Immunol.* 136(6):2026–2032 (Mar. 15, 1986).

Grossman, H. B., Clinical Applications of Monoclonal Antibody Technology, *Urologic Clinics of North America* 13(3):465–474 (Aug. 1986).

Harlan, J. M. et al., The Role of Neutrophil Membrane Glycoprotein GP-150 in Neutrophil Adherence to Endothelium In Vitro, *Blood* 66(1):167–178 (Jul. 1985).

Haskard, D. et al., T Lymphocyte Adhesion to Endothelial Cells: Mechanisms Demonstrated by Anti-LFA-1 Monoclonal Antibodies, *J. Immunol.* 137(9):2901–2906 (Nov. 1986).

Hogg, N. et al., The p150,95 molecule is a marker of human mononuclear phagocytes: comparison with expression of class II molecules, *Eur. J. Immunol.* 16:240–248 (1986).

Hynes, R. O. Integrins: A Family of Cell Surface Receptors, *Cell* 48:549–554 (Feb. 27, 1987).

Jones, D. H. et al., Subcellular Location of MAC-1 (CR-3) in Human Neutrophils: Effects of Chemotactic Factors and PMA, *Ped. Res.* 21:312a, Abstract No. 835 (1987).

Keizer, G. D. et al., Biochemical and functional characteristics of the human leukocyte membrane antigen family LFA-1, Mo-1, and p150,95, *Eur. J. Immunol.* 15:1142–1147 (1985).

Keizer, G. D. et al., Membrane Glycoprotein p150,95 of Human Cytotoxic T Cell Clones is Involved in Conjugate Formation with Target Cells, *J. Immunol.* 138(10):3130–3136 (May 15, 1987).

Keizer, G. D. et al., Role of p150,95 in adhesion, migration, chemotaxis and phagocytosis of human monocytes, *Eur. J. Immunol.* 17:1317–1322 (1987).

Khaw, B. A. et al., Myocardial Infarct Imaging of Antibodies to Canine Cardiac Myosin with Indium-111-Diethylenetriamine Pentaacetic Acid, *Science* 209:295–297 (Jul. 11, 1980).

King, J., Deciphering the Rules of Protein Folding, *C&EN*, pp. 32–54 (Apr. 10, 1989).

Kishimoto, T. K. et al., Cloning of the β Subunit of the Leukocyte Adhesion Proteins: Homology to an Extracellular Matrix Receptor Defines a Novel Supergene Family, *Cell* 48:681–690 (Feb. 27, 1987).

Kishimoto, T. K. et al., Cloning of the β Subunit of LFA-1 Mac-1, and p150,95: Homology to a fibronectin receptor and the molecular basis of leukocyte adhesion deficiency, *Fed. Proc.* 46:446, Abstract No. 755 (Mar. 1987).

Kishimoto, T. K. et al., The β Subunit of LFA-1, Mac-1, and p150,95: Gene Cloning, Homology to a Fibronectin Receptor, and the Molecular Basis of Leukocyte Adhesion Deficiency, *J. Cell. Biochem.*, Suppl. 11D, p. 271, Abstract No. T415 (1987).

(List continued on next page.)

OTHER PUBLICATIONS

Kohl, S. et al., The Genetic Deficiency of Leukocyte Surface Glycoprotein Mac-1, LFA-1, p150,95 in Humans is Associated with Defective Antibody-Dependent Cellular Cytotoxicity In Vitro and Defective Protection Against Herpes Simplex Virus Infection In Vivo, *J. Immunol.* 137:1688–1694 (Sep. 1, 1986).

Krensky, A. M. et al., LFA-1, LFA-2 and LFA-3 Antigens are Involved in CTL-Target Conjunction, *J. Immunol.* 132(5):2180–2182 (May 1984).

Lanier, L. L. et al., p.150/95, Third member of the LFA-1/CR$_3$ polypeptide family identified by anti-Leu M5 monoclonal antibody, *Eur. J. Immunol.* 15:713–718 (1985).

Lathe, R., Synthetic Oligonucleotide Probes Deduced from Amino Acid Sequence Data, Theoretical and Practical Considerations, *J. Mol. Biol.*, 183:1–12 (1985).

Marlin, S. D. et al., Purified Intercellular Adhesion Molecule-1 (ICAM-1) is a Ligand for Lymphocyte Function-Associated Antigen 1 (LFA-1), *Cell* 51:813–819 (Dec. 4, 1987).

Martz, E., Immune T Lymphocyte to Tumor Cell Adhesion, *J. Cell Biol.* 84:584–598 (Mar. 1980).

Micklem, K. J. et al., Isolation of complement-fragment-iC3b-binding proteins by affinity chromatography, Biochem. J. 231:233–236 (1985).

Miller, L. J. et al., Regulated Expression of the Mac-1, LFA-1, p150,95 Glycoprotein Family During Leukocyte Differentiation, *J. Immunol.* 137(9):2891–2900 (Nov. 1, 1986).

Mosser, D. M. et al., The Mouse Macrophage Receptor for C3bi (CR3) is a Major Mechanism in the Phagocytosis of Leishmania Promastigotes, *J. Immunol.* 135(4):2785–2789 (Oct. 1985).

Patarroyo, M. et al., Identification of a novel adhesion molecules in human leukocytes by monoclonal antibody LB-2, *FEBS Letters* 210(2):127–131 (Jan. 1987).

Patarroyo, M. et al., Identification of a Cell-Surface Glycoprotein Mediating Cell Adhesion in EBV-Immortalized Normal B Cells, *Int. J. Cancer* 38:539–547 (1986).

Pober, J. S. et al., Overlapping Patterns of Activation of Human Endothelial Cells by Interleukin 1, Tumor Necrosis Factor, and Immune Interferon, *J. Immunol. 137(6):1893–1896 (Sep. 15, 1986).*

Pohlman, T. H. et al., An Endothelial Cell Surface Factor(s) Induced In Vitro by Lipopolysaccharide, Inteleukin 1, and Tumor Necrosis Factor-$\alpha$ Increases Neutrophil Adherence by a CDw18-Dependent Mechanism, *J. Immunol.* 136(12):4548–4553 (Jun. 15, 1986).

Poltorak, M. et al., Myelin-associated Glycoprotein, a Member of the L2/HNK-1 Family of Neural Cell Adhesion Molecules, is Involved in Neuron-Oligodendrocyte and Oligodendrocyte-Oligodendrocyte Interaction, *J. Cell Biol.* 105:1893–1899 (Oct. 1987).

Pytela, R., Amino acid sequence of the murine Mac-1 $\alpha$ chain reveals homology with the integrin family and an additional domain related to von Willebrand factor, *EMBO J.* 7(5):1371–1738 (1988).

Rothlein, R. et al., A Human Intercellular Adhesion Molecules (ICAM-1) Distinct from LFA-1, *J. Immunol.* 137(4):1270–1274 (Aug. 15, 1986).

Rothlein, R. et al., The Requirement for Lymphocyte Function-Associated Antigen 1 In Homotypic Leukocyte Adhesion Stimulated by Phorbol Ester, *J. Exp. Med.* 163:1132–1149 (May 1986).

Ruoslahti, E. et al., New Perspectives in Cell Adhesion: RGD and Integrins, *Science* 238:491–497 (Oct. 23, 1987).

Salzer, J. L. et al., The Amino Acid Sequences of the Myelin-associated Glycoproteins: Homology to the Immunoglobulin Gene Superfamily, *J. Cell Biol.* 104:957–965 (Apr. 1987).

Sanchez-Madrid, F. et al., A Human Leukocyte Differentiation Antigen Family with Distinct $\alpha$-Subunits and a Common $\beta$-Subunit: The Lymphocyte Function-Associated Antigen (LFA-1), the C3bi Complement Receptor (OKM1/Mac-1), and the p150,95 Molecule, *J. Exp. Med.* 158:1785–1803 (Dec. 1983).

Sanchez-Madrid, F. et al., Mapping of Antigenic and Functional Epitopes on the $\alpha$- and $\beta$-Subunits of Two Related Mouse Glycoproteins Involved in Cell Interactions, LFA-1 and MAC-1, *J. Exp. Med.* 158:586–602 (Aug. 1983).

Sastre, L. et al., A partial genomic DNA clone for the $\alpha$ subunit of the mouse component receptor type 3 and cellular adhesion molecule Mac-1, *Proc. Natl. Acad. Sci. USA* 83:5644–5648 (Aug. 1986).

Schwarting, R. et al., The Monoclonal Antibodies $\alpha$S-HCL 1 ($\alpha$Leu-14) and $\alpha$S-HCL 3 ($\alpha$Leu-M5) Allow the Diagnosis of Hairy Cell Leukemia, *Blood* 65(4):974–983 (Apr. 1985).

(List continued on next page.)

OTHER PUBLICATIONS

Simpson, P. J. et al., Reduction of Experimental Canine Myocardial Reperfusion Injury by a Monoclonal Antibody (Anti-Mol, Anti-CD11b) That Inhibits Leukocyte Adhesion, *J. Clin. Invest.* 81:624–629 (Feb. 1988).

Smith, C. W. et al., Motility and Adhesiveness in Human Neutrophils, *J. Clin. Invest.* 63:221–229 (Feb. 1979).

Springer, T. et al., Mac-1: a macrophage differentiation antigen identified by monoclonal antibody, *Eur. J. Immunol.* 9:301–306 (1979).

Springer, T. A. et al., Inherited Deficiency of the Mac-1, LFA-1, p150,95 Glycoprotein Family and Its Molecular Basis, *J. Exp. Med.* 160:1901–1918 (Dec. 1984).

Springer, T. A. et al., LFA-1 and Lyt-2,3 Molecules Associated with T Lymphocyte-Mediated Killing; and Mac-1, an LFA-1 Homologue Associated with Complement Receptor Function, *Immunological Rev.* 68:171–195 (1982).

Springer, T. A. et al., The Lymphocyte Function-Associated LFA-1, CD2, and LFA-3 Molecules: Cell Adhesion Receptors of the Immune System, *Ann. Rev. Immunol.* 5:223–252 (1987).

Strassman, G. et al., Mechanisms of Tumor Cell Capture by Activated Macrophages: Evidence for Involvement of Lymphocyte Function-Associated (LFA)-1 Antigen, *J. Immunol.*, 136(11):4328–4333 (Jun. 1, 1986).

Supplementary European Search Report to accompany European Application No. 90905066.8, completed Oct. 30, 1991.

Todd III, R. F. et al., Subcellular Localization of the Large Subunit of Mol (Mol$_\alpha$; formerly gp 110), a Surface Glycoprotein Associated with Neutrophil Adhesion, *J. Clin. Invest.* 74:1280–1290 (Oct. 1984).

Todd III, R. F. et al., The CD11/CD18 Leukocyte Glycoprotein Deficiency, *Hematology/Oncology Clinics of North America* 2(1):13–31 (Mar. 1988).

Unger, E. C. et al., Magnetic Resonance Imaging Using Gadolinum Labeled Monoclonal Antibody, *Invest. Radiol.* 20:693–700 (Oct. 1985).

Vedder, N. B. et al., Increased Surface Expression of CD11b/CD18 (Mac-1) is not Required for Stimulated Neutrophil Adherence to Cultured Endothelium, *J. Clin. Invest.* 81:676–682 (Mar. 1988).

Wallis, W. J. et al., Human Monocyte Adherence to Cultured Vascular Endothelium: Monoclonal Antibody-Defined Mechanisms, *J. Immunol.* 135(4):2323–2330 (Oct. 1985).

Yancey, K. B. et al., Human C5a Modulats Monocyte Fc and C3 Receptor Expression, *J. Immunol.* 135(1):465–470 (Jul. 1985).

Yang, Y. et al., Human IL-3 (Multi-CSF): Identification by Expression Cloning of a Novel Hematopoietic Growth Factor Related to Murine IL-3, *Cell* 47:3–10 (Oct. 10, 1986).

Young, R. A. et al., Efficient isolation of genes by using antibody probes, *Proc. Natl. Acad. Sci. USA* 80:1194–1198 (Mar. 1983).

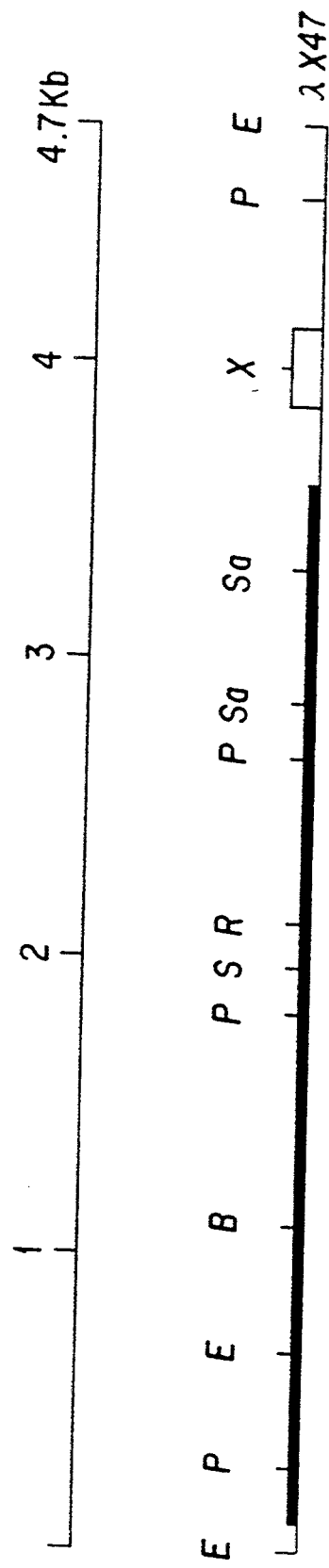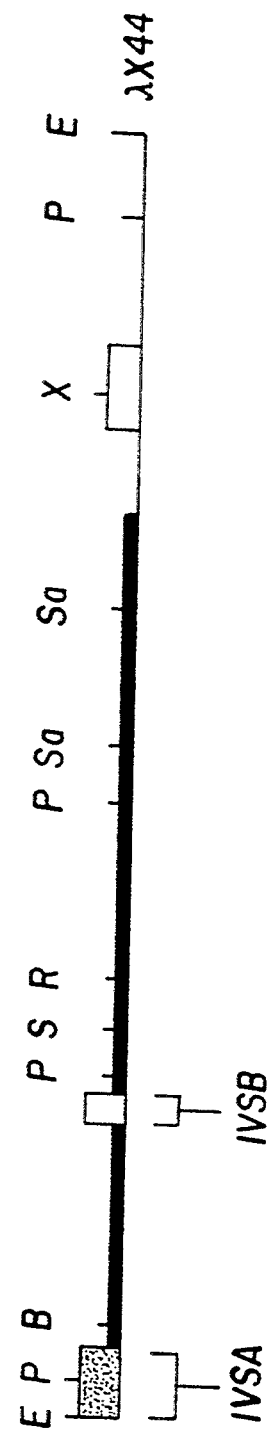
FIG. 2A
FIG. 2B

```
                GAATTCCTGCCACTCTTCCTGCAACGGCCCAGGAGCTCAGAGCTCCACATCTGACCTTCTAGTC      64
      65    ATG ACC AGG ACC AGG GCA GCA CTC CTC CTG TTC ACA GCC TTA
      -19   Met Thr Arg Thr Arg Ala Ala Leu Leu Leu Phe Thr Ala Leu
            GCA ACT TCT CTA GGT TTC AAC TTG GAC ACA GAG GAG CTG ACA GCC
            Ala Thr Ser Leu Gly Phe Asn Leu Asp Thr Glu Glu Leu Thr Ala       10
                            -1  +1
      152   TTC CGT GTG GAC AGC GCT GGG TTT GGA GAC AGC GTG GTC CAG
            Phe Arg Val Asp Ser Ala Gly Phe Gly Asp Ser Val Val Gln
                                N-terminus
            TAT GCC AAC TCC TGG GTG GTG GTT GGA GCC CCC CAA AAG ATA ACA
            Tyr Ala Asn Ser Trp Val Val Val Gly Ala Pro Gln Lys Ile Thr
                                                                              39
      238   GCT GCC AAC CAA ACG GGT GGC CTC TAC CAG TGT GGC TAC AGC
            Ala Ala Asn Gln Thr Gly Gly Leu Tyr Gln Cys Gly Tyr Ser
            ACT GGT GCC TGT GAG CCC ATC GGC CTG CAG GTG CCC CCG GAG GCC
            Thr Gly Ala Cys Glu Pro Ile Gly Leu Gln Val Pro Pro Glu Ala       68
      325   GTG AAC ATG TCC CTG GGC CTG TCC CTG GCG TCT ACC ACC AGC
            Val Asn Met Ser Leu Gly Leu Ser Leu Ala Ser Thr Thr Ser
            CCT TCC CAG CTG CTG GCC TGC GGC CCC ACC GTG CAC CAC GAG TGC
            Pro Ser Gln Leu Leu Ala Cys Gly Pro Thr Val His His Glu Cys       97
      412   GGG AGG AAC ATG TAC CTC ACC GGA CTC TGC TTC CTC CTG GGC
            Gly Arg Asn Met Tyr Leu Thr Gly Leu Cys Phe Leu Leu Gly
            CCC ACC CAG CTC ACC CAG AGG CTC CCG GTG TCC AGG CAG GAG TGC
            Pro Thr Gln Leu Thr Gln Arg Leu Pro Val Ser Arg Gln Glu Cys       126
      499   CCA AGA CAG GAG CAG GAC ATT GTG TTC CTG ATC GAT GGC TCA
            Pro Arg Gln Glu Gln Asp Ile Val Phe Leu Ile Asp Gly Ser
            GGC AGC ATC TCC TCC CGC AAC TTT GCC ACG ATG ATG AAC TTC GTG
            Gly Ser Ile Ser Ser Arg Asn Phe Ala Thr Met Met Asn Phe Val       155
      587   AGA GCT GTG ATA AGC CAG TTC CAG AGA CCC AGC ACC CAG TTT
            Arg Ala Val Ile Ser Gln Phe Gln Arg Pro Ser Thr Gln Phe
                        125a
            TCC CTG ATG CAG TTC TCC AAC AAA TTC CAA ACA CAC TTC ACT TTC
            Ser Leu Met Gln Phe Ser Asn Lys Phe Gln Thr His Phe Thr Phe       184
      674   GAG GAA TTC AGG CGC ACG TCA AAC CCC CTC AGC CTG TTG GCT
            Glu Glu Phe Arg Arg Thr Ser Asn Pro Leu Ser Leu Leu Ala
            TCT GTT CAC CAG CTG CAA GGG TTT ACA TAC ACG GCC ACC GCC ATC
            Ser Val His Gln Leu Gln Gly Phe Thr Tyr Thr Ala Thr Ala Ile       213
                        122
      761   CAA AAT GTC GTG CAC CGA TTG TTC CAT GCC TCA TAT GGG GCC
            Gln Asn Val Val His Arg Leu Phe His Ala Ser Tyr Gly Ala
```

FIG. 3a

```
             CGT AGG GAT GCC ACC AAA ATT CTC ATT GTC ATC ACT GAT GGG AAG
             Arg Arg Asp Ala Thr Lys Ile Leu Ile Val Ile Thr Asp Gly Lys       242

848    AAA GAA GGC GAC AGC CTG GAT TAT AAG GAT GTC ATC CCC ATG
             Lys Glu Gly Asp Ser Leu Asp Tyr Lys Asp Val Ile Pro Met

GCT GAT GCA GCA GGC ATC ATC CGC TAT GCA ATT GGG GTT GGA TTA
             Ala Asp Ala Ala Gly Ile Ile Arg Tyr Ala Ile Gly Val Gly Leu       271
                                               ―――――――――――――――――――
                                                         60b
      935    GCT TTT CAA AAC AGA AAT TCT TGG AAA GAA TTA AAT GAC ATT
             Ala Phe Gln Asn Arg Asn Ser Trp Lys Glu Leu Asn Asp Ile
             ―――――――――――

GCA TCG AAG CCC TCC CAG GAA CAC ATA TTT AAA GTG GAG GAC TTT
             Ala Ser Lys Pro Ser Gln Glu His Ile Phe Lys Val Glu Asp Phe       300
                                                        ―――――――――――――
     1022    GAT GCT CTG AAA GAT ATT CAA AAC CAA CTG AAG GAG AAG ATC
             Asp Ala Leu Lys Asp Ile Gln Asn Gln Leu Lys Glu Lys Ile
             ―――――――――――――――――――――――――――――――――――
                       72b
             TTT GCC ATT GAG GGT ACG GAG ACC ACA AGC AGT AGC TCC TTC GAA
             Phe Ala Ile Glu Gly Thr Glu Thr Thr Ser Ser Ser Ser Phe Glu       329

1109    TTG GAG ATG GCA CAG GAG GGC TTC AGC GCT GTG TTC ACA CCT
             Leu Glu Met Ala Gln Glu Gly Phe Ser Ala Val Phe Thr Pro

GAT GGC CCC GTT CTG GGG GCT GTG GGG AGC TTC ACC TGG TCT GGA
             Asp Gly Pro Val Leu Gly Ala Val Gly Ser Phe Thr Trp Ser Gly       358

1196    GGT GCC TTC CTG TAC CCC CCA AAT ATG AGC CCT ACC TTC ATC
             Gly Ala Phe Leu Tyr Pro Pro Asn Met Ser Pro Thr Phe Ile
                                         ―――――――――――

AAC ATG TCT CAG GAG AAT GTG GAC ATG AGG GAC TCT TAC CTG GGT
             Asn Met Ser Gln Glu Asn Val Asp Met Arg Asp Ser Tyr Leu Gly       387
             ―――――――――――                         ―――――――――――――――――――
     1283    TAC TCC ACC GAG CTG GCC CTC TGG AAA GGG GTG CAG AGC CTG
             Tyr Ser Thr Glu Leu Ala Leu Trp Lys Gly Val Gln Ser Leu
             ―――――――――――――――――――――――
                       79a
             GTC CTG GGG GCC CCC CGC TAC CAG CAC ACC GGG AAG GCT GTC ATC
             Val Leu Gly Ala Pro Arg Tyr Gln His Thr Gly Lys Ala Val Ile       416

1370    TTC ACC CAG GTG TCC AGG CAA TGG AGG ATG AAG GCC GAA GTC
             Phe Thr Gln Val Ser Arg Gln Trp Arg Met Lys Ala Glu Val

ACG GGG ACT CAG ATC GGC TCC TAC TTC GGG GCC TCC CTC TGC TCC
             Thr Gly Thr Gln Ile Gly Ser Tyr Phe Gly Ala Ser Leu Cys Ser       445

1457    GTG GAC GTA GAC ACC GAC GGC AGC ACC GAC CTG GTC CTC ATC
             Val Asp Val Asp Thr Asp Gly Ser Thr Asp Leu Val Leu Ile

GGG GCC CCC CAT TAC TAC GAG CAG ACC CGA GGG GGC CAG GTG TCT
             Gly Ala Pro His Tyr Tyr Glu Gln Thr Arg Gly Gly Gln Val Ser       474

1544    GTG TGT CCC TTG CCC AGG GGG TGG AGA AGG TGG TGG TGT GAT
             Val Cys Pro Leu Pro Arg Gly Trp Arg Arg Trp Trp Cys Asp
```

FIG. 3b

```
          GCT GTT CTC TAC GGG GAG CAG GGC CAC CCC TGG GGT CGC TTT GGG
          Ala Val Leu Tyr Gly Glu Gln Gly His Pro Trp Gly Arg Phe Gly          503
1631      GCG GCT GTG ACA GTG CTG GGG GAT GTG AAT GGG GAC AAG CTG
          Ala Ala Leu Thr Val Leu Gly Asp Val Asn Gly Asp Lys Leu
                                  90b
          ACA GAC GTG GTC ATC GGG GCC CCA GGA GAG GAG GAG AAC CGG GGT
          Thr Asp Val Val Ile Gly Ala Pro Gly Glu Glu Glu Asn Arg Gly          532
1718      GCT GTC TAC CTG TTT CAC GGA GTC TTG GGA CCC AGC ATC AGC
          Ala Val Tyr Leu Phe His Gly Val Leu Gly Pro Ser Ile Ser
                                      70
          CCC TCC CAC AGC CAG CGG ATC GCG GGC TCC CAG CTC TCC TCC AGG
          Pro Ser His Ser Gln Arg Ile Ala Gly Ser Gln Leu Ser Ser Arg         561
1805      CTG CAG TAT TTT GGG CAG GCA CTG AGC GGG GGT CAA GAC CTC
          Leu Gln Tyr Phe Gly Gln Ala Leu Ser Gly Gly Gln Asp Leu
                                                      90a
          ACC CAG GAT GGA CTG GTG GAC CTG GCT GTG GGG GCC CGG GGC CAG
          Thr Gln Asp Gly Leu Val Asp Leu Ala Val Gly Ala Arg Gly Gln         590
1892      GTG CTC CTG CTC AGG ACC AGA CCT GTG CTC TGG GTG GGG GTG
          Val Leu Leu Leu Arg Thr Arg Pro Val Leu Trp Val Gly Val

AGC ATG CAG TTC ATA CCT GCC GAG ATC CCC AGG TCT GCG TTT GAG
          Ser Met Gln Phe Ile Pro Ala Glu Ile Pro Arg Ser Ala Phe Glu         619
                          97
1979      TGT CGG GAG CAG GTG GTC TCT GAG CAG ACC CTG GTA CAG TCC
          Cys Arg Glu Gln Val Val Ser Glu Gln Thr Leu Val Gln Ser

AAC ATC TGC CTT TAC ATT GAC AAA CGT TCT AAG AAC CTG CTT GGG
          Asn Ile Cys Leu Tyr Ile Asp Lys Arg Ser Lys Asn Leu Leu Gly         648
2066      AGC CGT GAC CTC CAA AGC TCT GTG ACC TTG GAC CTG GCC CTC
          Ser Arg Asp Leu Gln Ser Ser Val Thr Leu Asp Leu Ala Leu

GAC CCT GGC CGC CTG AGT CCC CGT GCC ACC TTC CAG GAA ACA AAG
          Asp Pro Gly Arg Leu Ser Pro Arg Ala Thr Phe Gln Glu Thr Lys        677
2153      AAC CGG AGT CTG AGC CGA GTC CGA GTC CTC GGG CTG AAG GCA
          Asn Arg Ser Leu Ser Arg Val Arg Val Leu Gly Leu Lys Ala

CAC TGT GAA AAC TTC AAC CTG CTG CTC CCG AGC TGC GTG GAG GAC
          His Cys Glu Asn Phe Asn Leu Leu Leu Pro Ser Cys Val Glu Asp        706
2240      TCT GTG ACC CCC ATT ACC TTG CGT CTG AAC TTC ACG CTG GTG
          Ser Val Thr Pro Ile Thr Leu Arg Leu Asn Phe Thr Leu Val

GGC AAG CCC CTC CTT GCC TTC AGA AAC CTG CGG CCT ATG CTG GCC
          Gly Lys Pro Leu Leu Ala Phe Arg Asn Leu Arg Pro Met Leu Ala        735
```

FIG. 3c

| | | |
|---|---|---|
| 2327 | GCA CTG GCT CAG AGA TAC TTC ACG GCC TCC CTA CCC TTT GAG<br>Ala Leu Ala Gln Arg <u>Tyr Phe Thr Ala Ser Leu Pro Phe Glu</u><br>60a | |
| | AAG AAC TGT GGA GCC GAC CAT ATC TGC CAG GAC AAT CTC GGC ATC<br><u>Lys</u> Asn Cys Gly Ala Asp His Ile Cys Gln Asp Asn Leu Gly Ile | 764 |
| 2414 | TCC TTC AGC TTC CCA GGC TTG AAG TCC CTG CTG GTG GGG AGT<br>Ser Phe Ser Phe Pro Gly Leu Lys Ser Leu Leu Val Gly Ser | |
| | AAC CTG GAG CTG AAC GCA GAA GTG ATG GTG TGG AAT GAC GGG GAA<br>Asn Leu Glu Leu Asn Ala Glu Val Met Val Trp Asn Asp Gly Glu | 793 |
| 2501 | GAC TCC TAC GGA ACC ACC ATC ACC TTC TCC CAC CCC GCA GGA<br>Asp Ser Tyr Gly Thr Thr Ile Thr Phe Ser His Pro Ala Gly | |
| | CTG TCC TAC CGC TAC GTG GCA GAG GGC CAG AAA CAA GGG CAG CTG<br>Leu Ser Tyr Arg Tyr Val Ala Glu Gly Gln Lys Gln Gly Gln Leu | 822 |
| 2588 | CGT TCC CTG CAC CTG ACA TGT GAC AGC GCC CCA GTT GGG AGC<br>Arg Ser Leu His Leu Thr Cys Asp Ser Ala Pro Val Gly Ser | |
| | CAG GGC ACC TGG AGC ACC AGC TGC AGA ATC AAC CAC CTC ATC TTC<br>Gln Gly Thr Trp Ser Thr Ser Cys Arg Ile Asn His Leu Ile Phe | 851 |
| 2675 | CGT GGC GGC GCC CAG ATC ACC TTC TTG GCT ACC TTT GAC GTC<br>Arg Gly Gly Ala Gln Ile Thr Phe Leu Ala Thr Phe Asp Val | |
| | TCC CCC AAG GCT GTC CTG GGA GAC CGG CTG CTT CTG ACA GCC AAT<br>Ser Pro Lys Ala Val Leu Gly Asp Arg Leu Leu Leu Thr Ala <u>Asn</u> | 880 |
| 2762 | GTG AGC AGT GAG AAC AAC ACT CCC AGG ACC AGC AAG ACC ACC<br><u>Val Ser</u> Ser Glu <u>Asn Asn Thr</u> Pro Arg Thr Ser Lys <u>Thr Thr</u> | |
| | TTC CAG CTG GAG CTC CCG GTG AAG TAT GCT GTC TAC ACT GTG GTT<br><u>Phe Gln Leu Glu Leu Pro Val Lys</u> Tyr Ala Val Tyr Thr Val Val<br>63a | 909 |
| 2849 | AGC AGC CAC GAA CAA TTC ACC AAA TAC CTC AAC TTC TCA GAG<br>Ser Ser His Glu Gln Phe Thr Lys Tyr Leu <u>Asn Phe Ser</u> Glu | |
| | TCT GAG GAG AAG GAA AGC CAT GTG GCC ATG CAC AGA TAC CAG GTC<br>Ser Glu Glu Lys Glu Ser His Val Ala Met His Arg Tyr Gln Val | 938 |
| 2936 | AAT AAC CTG GGA CAG AGG GAC CTG CCT GTC AGC ATC AAC TTC<br>Asn Asn Leu Gly Gln Arg <u>Asp Leu Pro Val Ser Ile Asn Phe</u> | |
| | TGG GTG CCT GTG GAG CTG AAC CAG GAG GCT GTG TGG ATG GAT GTG<br><u>Trp Val Pro Val Glu Leu Asn Gln Glu Ala Val Trp Met Asp Val</u><br>114 | 967 |
| 3023 | GAG GTC TCC CAC CCC CAG AAC CCA TCC CTT CGG TGC TCC TCA<br><u>Glu Val</u> Ser His Pro Gln Asn Pro Ser Leu Arg Cys Ser Ser | |

FIG. 3d

```
          GAG AAA ATC GCA CCC CCA GCA TCT GAC TTC CTG GCG CAC ATT CAG
          Glu Lys Ile Ala Pro Pro Ala Ser Asp Phe Leu Ala His Ile Gln      996

3110      AAG AAT CCC GTG CTG GAC TGC TCC ATT GCT GGC TGC CTG CGG
          Lys Asn Pro Val Leu Asp Cys Ser Ile Ala Gly Cys Leu Arg

TTC CGC TGT GAC GTC CCC TCC TTC AGC GTC CAG GAG GAG CTG GAT
          Phe Arg Cys Asp Val Pro Ser Phe Ser Val Gln Glu Glu Leu Asp    1025

3197      TTC ACC CTG AAG GGC AAC CTC AGC TTT GGC TGG GTC CGC CAG
          Phe Thr Leu Lys Gly Asn Leu Ser Phe Gly Trp Val Arg Gln

ATA TTG CAG AAG AAG GTG TCG GTC GTG AGT GTG GCT GAA ATT ACG
          Ile Leu Gln Lys Lys Val Ser Val Val Ser Val Ala Glu Ile Thr    1054

3284      TTC GAC ACA TCC GTG TAC TCC CAG CTT CCA GGA CAG GAG GCA
          Phe Asp Thr Ser Val Tyr Ser Gln Leu Pro Gly Gln Glu Ala

TTT ATG AGA GCT CAG ACG ACA ACG GTG CTG GAG AAG TAC AAG GTC
          Phe Met Arg Ala Gln Thr Thr Thr Val Leu Glu Lys Tyr Lys Val    1083

3371      CAC AAC CCC ACC CCC CTC ATC GTA GGC AGC TCC ATT GGG GGT
          His Asn Pro Thr Pro Leu Ile Val Gly Ser Ser Ile Gly Gly
                          133
          CTG TTG CTG CTG GCA CTC ATC ACA GCG GTA CTG TAC AAA GTT GGC
          Leu Leu Leu Leu Ala Leu Ile Thr Ala Val Leu Tyr Lys Val Gly    1112

3485      TTC TTC AAG CGT CAG TAC AAG GAA ATG ATG GAG GAG GCA AAT
          Phe Phe Lys Arg Gln Tyr Lys Glu Met Met Glu Glu Ala Asn

GGA CAA ATT GCC CCA GAA AAC GGG ACA CAG ACC CCC AGC CCG CCC
          Gly Gln Ile Ala Pro Glu Asn Gly Thr Gln Thr Pro Ser Pro Pro    1141

3545      AGT GAG AAA TGA TCC CTC TTT GCC TTG GAC TTC TTC TCC CGC
          GAT TTT CCC CAC TTA CTT ACC CTC ACC TGT CAG GCT GAC GGG GAG
          Ser Glu Lys ***

3632      GAACCACTGCACCACCGAGAGAGGCTGGGATGGGCCTGCTTCCTGTCTTTGGGAG

AAAACGTCTTGCTTGGGAAGGGGCCTTTGTCTTGTCAAGGTTCCAACTGGAAACCCTTAG

GACAGGGTCCCTGCTGTGTTCCCCAAAAGGACTTGACTTGCAATTTCTACCTAGA

AATACATGGACAATACCCCCAGGCCTCAGTCTCCCTTCTCCCATGAGGCACGAATGATCT

3862      TTCTTTCCTTTCCTTTTTTTTTTTTTTCTTTTCTTTTTTTTTTTTTTGAGACGG

AGTCTCGCTCTGTCACCCAGGCTGGAGTGCAATGGCGTGATCTCGGCTCGCTGCAACCTC

CGCCTCCCGGGTTCAAGTAATTCTGCTGTCTCAGCCTCCTGCGTAGCTGGGACTA

CAGGCACACGCCACCTCGCCCGGCCCGATCTTTCTAAAATACAGTTCTGAATATGCTGCT

4092      CATCCCCACCTGTCTTCAACAGCTCCCCATTACCCTCAGGACAATGTCTGAACTC
```

FIG. 3e

TCCAGCTTCGCGTGAGAAGTCCCCTTCCATCCCAGAGGGTGGGCTTCAGGGCGCACAGCA

TGAGAGCCTCTGTGCCCCCATCACCCTCGTTTCCAGTGAATTAGTGTCATGTCAG

CATCAGCTCAGGGCTTCATCGTGGGGCTCTCAGTTCCGATTCCCCAGGCTGAATTGGGAG

4322    TGAGATGCCTGCATGCTGGGTTCTGCACAGCTGGCCTCCCGCGGTTGGGTCAACA

TTGCTGGCCTGGAAGGGAGGAGCGCCCTCTAGGGAGGGACATGGCCCCGGTGCGGCTGCA

GCTCACCAGCCCCAGGGGCAGAAGAGACCCAACCACTTCCTATTTTTTGAGGCTA

TGAATATAGTACCTGAAAAAATGCCAAGCACTAGATTATTTTTTTAAAAAGCGTACTTTA

4552    AATGTTTGTGTTAATACACATTAAAACATCGCACAAAAACGATGCATCTACCGCT

CCTTGGGAAATAATCTGAAAGGTCTAAAAATAAAAAGCCTTCTGTGGAAAAAAAAAAAA

AAAAAAAAAAAAAAAAAAAAAAAAAAAAAAAAAAAAAA    4704

FIG. 3f

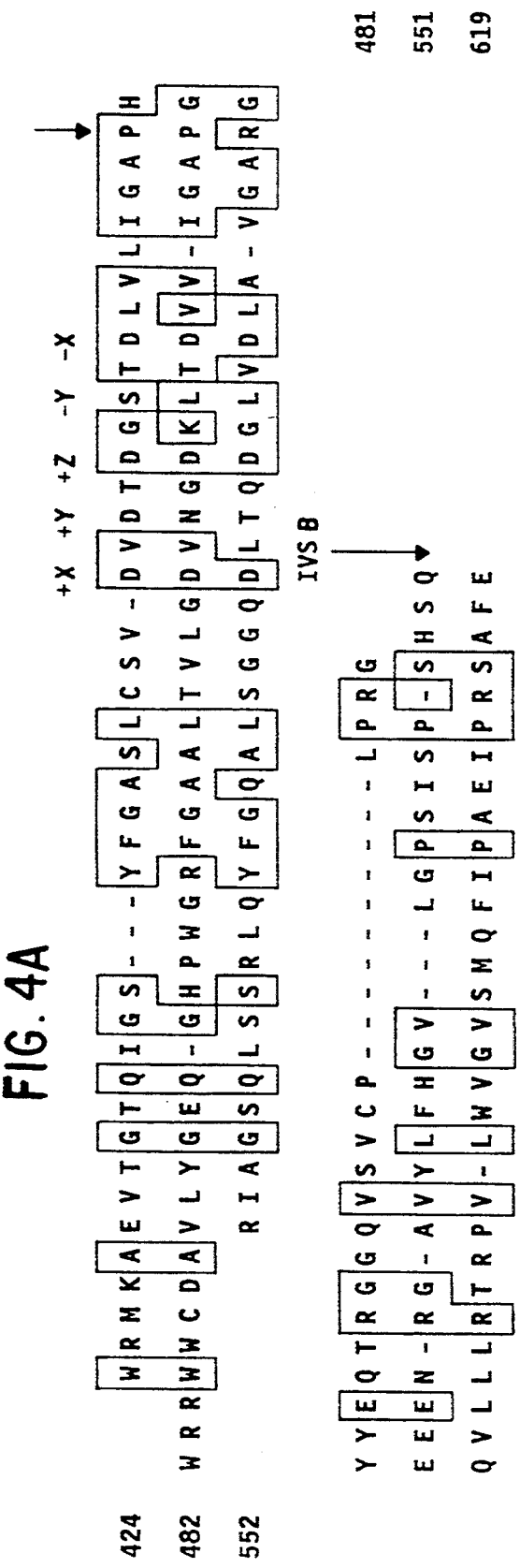

DIVALENT CATION–BINDING SITES

| PROTEIN | RESIDUE # | AMINOACID SEQUENCE | | | | | | | | | | |
|---|---|---|---|---|---|---|---|---|---|---|---|---|
| p150,95 ALPHA | 446 | V | D | V | D | T | D | G | S | T | D | L V L |
| | 510 | G | D | V | N | G | D | K | L | T | D | V V I |
| | 573 | Q | D | L | T | Q | D | G | L | V | D | L A V |
| PARVALBUMIN CD | 50 | I | D | E | D | K | S | G | F | I | E | E D E |
| EF | 89 | G | D | S | D | G | D | G | K | I | G | V D E |
| CALMODULIN I | 19 | F | D | K | D | G | N | G | T | I | T | T K E |
| II | 55 | V | D | A | D | G | N | G | T | I | N | F P E |
| III | 92 | F | D | K | D | G | N | G | Y | I | S | A A E |
| IV | 128 | A | N | I | D | G | D | G | E | V | N | Y E E |
| TROPONIN C | 26 | F | D | A | D | G | G | G | D | I | S | V K E |
| | 62 | V | D | E | D | G | S | G | T | I | D | F E E |
| | 102 | F | D | R | N | A | D | G | Y | I | D | P E E |
| | 138 | G | D | K | N | N | D | G | R | I | D | F D E |
| COORDINATION AXES | | +X | | +Y | | +Z | | | −Y | | −X | −Z |

```
p150,95   - A E I T F D T S V - - Y S Q L P G Q E A F M R A Q T T T V L E
IIb       Q S H A W F N V S - L P Y A V P L S L P R G E A Q V W T Q L
VNR       K S S A S F N V I E F P Y K N L P I E D I T N S T L V T T N V
FNR       Q C E A V Y K A L K M P Y R I L P R Q L P Q K E R Q V A T A V p150,95   E K Y K V H N - - P T P L I V G S S I - - G G L L L L A L I       1104
IIb       L R A L E E R A I P I W W V L V - G V L G G L L L L T I L       983
VNR       T W G I Q P A P M P V P V W V I L A V L A G L L L L A V L       599
FNR       Q W T K A E G S Y G V P L W I I L A I L F G L L L L G L L       195 p150,95   T A V L Y K V G F F K R Q - - Y K E M M E E A N G Q I A P - -    1144
IIb       V L A M W K V G F F K R N R P P L - - E E D D E E G E           1008
VNR       V F V R M G F F K R V R P P Q - - E E Q E R E Q L Q P H         636
FNR       I Y I T L Y K L G F F K R S L P Y G T A M E K A Q L K - P A T  228 p150,95   E N G T Q T P S P P S E K
IIb       E N G E G N S E T
VNR
FNR       S D A
```

ISOLATED NUCLEIC ACID ENCODING THE ALPHA SUBUNIT OF THE HUMAN LEUKOCYTE ADHESION RECEPTOR

CROSS-REFERENCE TO RELATED APPLICATIONS

This application is a continuation, of application Ser. No. 07/920,533, filed Jul. 28, 1992, now abandoned, which is a continuation of application Ser. No. 07/321,018, fled Mar. 9, 1989, now abandoned, which is a continuation-in-part of U.S. patent application Ser. No. 07/133,399; filed on Dec. 15, 1987, now abandoned.

FIELD OF THE INVENTION

The present invention relates to the leukocyte adhesion receptor p150,95. The invention further pertains to the cloning of DNA sequences which encode the alpha-subunit of this molecule. This invention was made in part with government support. The government has certain rights in this invention.

DESCRIPTION OF THE RELATED ART

The immune system is responsible for protecting an animal from foreign invaders, such as bacteria, viruses, etc. An excellent review of the defense system is provided by Eisen, H. W. (In: *Microbiology*, 3rd Ed., Harper & Row, Philadelphia, Pa. (1980), pp. 290–295 and 381–418). The ability of the immune system to protect an animal against foreign invaders depends, in large measure, on the presence and function of blood cells known as leukocytes. The ability of leukocytes to provide such protection has been found to require that these cells adhere to cellular and extracellular substrates.

For example, leukocytes mast be able to attach to endothelial cells so that they can migrate from circulation to sites of ongoing inflammation. Furthermore, they must attach to antigen-presenting cells so that a normal immune response can occur. They must also be able to attach to appropriate target cells so that the lysis of virally-infected (or tumor) cells can occur. Furthermore, leukocytes must be able to attach to various activated proteins (such as iC3b—the activated form of the third component of complement) so that they may efficiently phagocytose and clear microbial and cellular debris. Thus leukocyte adhesion is a requisite of a normally functioning host defense system. The inhibition of this defense system is desirable in cases such as transplantation, because the host "sees" the transplanted tissue as foreign and initiates an immune response to that tissue. Leukocyte adhesion is, therefore, also involved in the rejection of transplanted tissue and organs. Thus, an understanding of leukocyte adhesion may enable one to either augment an animal's ability to fight infection or suppress an animal's capacity to reject transplanted tissue.

Recently, leukocyte surface molecules involved in mediating leukocyte adhesion were identified using hybridoma technology. Briefly, monoclonal antibodies directed against human T-cells (Davignon, D., et al., *Proc. Natl. Acad. Sci. USA* 78:4535–4539 (1981)) and mouse spleen cells (Springer, T., et al., *Eur. J. Immunol.* 9:301–306 (1979)) were identified which bound to leukocyte surfaces and inhibited the attachment-related functions described above (Springer, T., et al., *Fed. Proc.* 44:2660–2663 (1985)). The molecules which were recognized by these antibodies comprise a set of leukocyte adhesion receptors known as the "Lymphocyte Function-Associated Antigen-1 family" (or the "LFA-1 family") of adhesion receptor molecules.

The LFA-1 family of adhesion receptor molecules contains three highly related cell surface glycoproteins. These glycoproteins have been found to mediate cell-cell interactions in inflammation. The glycoproteins have been designated "LFA-1" (lymphocyte function-associated antigen-1), "Mac-1" and "p150,95." Whereas LFA-1 is found on the surfaces of most leukocytes (Springer, T. A., et al., *Immunol. Rev.* 68:111–135 (1982)), Mac-1 and p150,95 are found primarily on macrophages, granulocytes and other large granular lymphocytes (Springer, T. A., et al., *Immunol. Rev.* 68:111–135 (1982); Keizer, G., et al., *Eur. J. Immunol.* 15:1142–1147 (1985)).

The LFA-1 glycoprotein family is composed of heterodimers, each containing an alpha-subunit which is non-covalently associated with a beta-subunit. The alpha-subunits of the family have been found to differ from one another and are designated CD11a, CD11b, and CD11c, respectively. The glycosylated alpha-subunits have approximate molecular weights of 180, 170, and 150 kd, respectively. In contrast, the beta-subunit of the LFA-1 family of adhesion receptors has been found to be identical, and to have a molecular weight of 95 kd (Sanchez-Madrid, F., et al., *J. Exper. Med.* 158:1785–1803 (1983); Keizer, G. D., et al., *Eur. J. Immunol.* 15:1142–1147 (1985); Springer, T., *Fed. Proc.* 44:2660–2663 (1985); Sanchez-Madrid, F., et al., *J. Exper. Med.* 158:586–602 (1983)).

Although the alpha-subunits of the glycoproteins do not exhibit the extensive homology shared by the beta-subunits, close analysis of the alpha-subunits of the glycoproteins has revealed that there are substantial similarities between them. Reviews of the similarities between the alpha and beta-subunits of the adhesion molecule glycoprotein family are provided by Sanchez-Madrid, F., et al. (*J. Exper. Med.* 158:586–602 (1983); *J. Exper. Med.* 158:1785–1803 (1983); Miller, L. J., et al., *J. Immunol.* 138:2381–2383 (1987)).

The importance of the LFA-1 family of receptors was initially recognized in studies which showed the ability of monoclonal antibodies (which were capable of binding to either the specific alpha-subunits, or the common beta-subunit) to inhibit adhesion-dependent leukocyte functions (Sanchez-Madrid, F., et al., *Proc. Natl. Acad. Sci. USA* 79:7489–7493 (1982); Beller, D. I., et al., *J. Exper. Med.* 156:1000–1009 (1982)).

Recently, a group of individuals has been identified who are unable to express normal amounts of any member of the LFA-1 adhesion protein family on their leukocyte cell surfaces. This disease has been termed "Leukocyte Adhesion Deficiency" or "LAD" and is characterized by chronic and recurring infections, as well as other clinical symptoms (Anderson, D.C., et al., *Fed. Proc.* 44:2671–2677 (1985); Anderson, D.C., et al., *J. Infect. Dis.* 152:668–689 (1985)). Leukocytes from LAD patients displayed in vitro defects which were similar to those observed when leukocytes of normal individuals were antagonized by antibody specific for members of the LFA-1 family. LAD patients were found to be unable to mount a normal immune response. This failure was found to be due to an inability of the leukocytes of LAD paients to adhere to cellular and extracellular substrates (Anderson, D.C., et al., *Fed. Proc.* 44:2671–2677 (1985); Anderson, D.C., et al., *J. Infect.*

Dis. 152:668–689 (1985)). These studies show that inflammatory reactions are mitigated when leukocytes are unable to adhere in a normal fashion due to the lack of functional adhesion molecules on their cell surface.

Thus, in summary, the ability of leukocytes to maintain the health and viability of an animal requires that they be capable of adhering to other cells (such as endothelial cells) and proteins (such as iC3b). This adherence has been found to require contacts which involve specific receptor molecules present on the leukocyte surface of the leukocytes. These cell surface receptor molecules have been found to be highly related to one another. Humans whose leukocytes lack these cell surface receptor molecules exhibit chronic and recurring infections, as well as other clinical symptoms.

Since leukocyte adhesion is involved in the process through which foreign tissue is identified and rejected, an understanding of this process is of significant value in the fields of organ transplantation, tissue grafts, allergy and oncology.

SUMMARY OF THE INVENTION

The present invention relates to leukocyte cell surface adhesion receptor molecules, and in particular, to the cloning and expression of the alpha-subunit of the p150,95 receptor molecule through the use of recombinant DNA technology. The invention pertains to the adhesion molecule itself, to functional fragments of the molecule, to nucleic acid (i.e., DNA, and especially cDNA) capable of encoding these receptor molecules, and to plasmids which contain such nucleic acid sequences. The present invention additionally encompasses methods for producing the receptor molecules which employ recombinant DNA technology.

In detail, the invention provides a polypeptide, substantially free of natural contaminants, selected from the group consisting of: (1) the alpha-subunit of p150,95; and (2) a functional derivative of the alpha-subunit of p150,95.

The invention additionally concerns a recombinant nucleic acid molecule which contains an oligonucleotide that encodes a polypeptide selected from the group consisting of: (1) the alpha-subunit of p150,95; and (2) a functional derivative of the alpha-subunit of p150,95.

The invention also includes a method of treating inflammation which comprises providing to a subject in need of such treatment an amount of an anti-inflammatory agent sufficient to suppress the inflammation; wherein the anti-inflammatory agent comprises a compound selected from the group consisting of: (1) the alpha-subunit of p150,95; and (2) a functional derivative of the alpha-subunit of p150,95.

The invention also includes the embodiment of the above-described method wherein the anti-inflammatory agent additionally contains a beta-subunit of a member of the LFA-1 family of receptor molecules.

The invention also includes the above-described methods of treating inflammation wherein the inflammation is associated with a condition selected from the group consisting of: delayed-type hypersensitivity; a symptom of an autoimmune disease; Reynaud's syndrome; autoimmune thyroiditis; EAE; multiple sclerosis; rheumatoid arthritis; lupus erythematosus; organ transplant rejection; tissue graft rejection; adult respiratory distress syndrome; multiple organ injury syndrome secondary to septicemia; multiple organ injury syndrome secondary to trauma; reperfusion injury of tissue; acute glomerulonephritis; reactive arthritis; dermatosis with acute inflammatory components; a central nervous system inflammatory disorder; thermal injury; hemodialysis; leukapheresis; ulcerative colitis; Crohn's disease; necrotizing enterocolitis; granulocyte transfusion associated syndrome; cytokine-induced toxicity and asthma.

BRIEF DESCRIPTION OF THE FIGURES

FIG. 2 shows a restriction map of p150,95 alpha-subunit cDNA clone λX47 (A) and λX44 (B). Restriction sites are EcoRI (E), BglII (B), Pst I (P), Sph I (S), Rsa I (R), Sac I (Sa), and Xma I (X). The opening reading frame is indicated as a thick line. The empty boxes represent Alu sequences. The position of two intervening sequences (IVS) in λX44 is indicated.

FIG. 3 shows the nucleotide and derived amino acid sequence of the p150,95 alpha-subunit of cDNA clone λX47. The N-terminus sequence and tryptic peptide sequences are underlined. The signal sequence and transmembrane domain are underlined with dashes. Putative N-glycosylation sites are double underlined. The partial Alu sequence in the 3' untranslated region is underlined. The polyadenylation signal is boxed.

FIG. 4 shows homologous repeats and intervening sequences in the p150,95 alpha-subunit gene. Panel A shows the presence of homologous tandem repeats. Common residues are boxed. "IVS B" indicates the position of intervening sequence B. The putative coordination of the divalent cation-binding sites are indicated. The proline after the metal ion-binding sites is indicated by an arrow. Panel B shows the nucleotide sequences of the intervening sequences, IVS A and IVS B, which were detected in the incompletely spliced λX44 cDNA clone. The coding and non-coding regions are separated by a slash. The deduced amino acid sequence of the coding regions is shown.

FIG. 5 shows the putative cation-binding sequences of the p150,95 alpha-subunit as compared with the sequences of known calcium and/or magnesium-binding sites of parvalbumin, tropronin C and calmodulin.

Figure 6A:
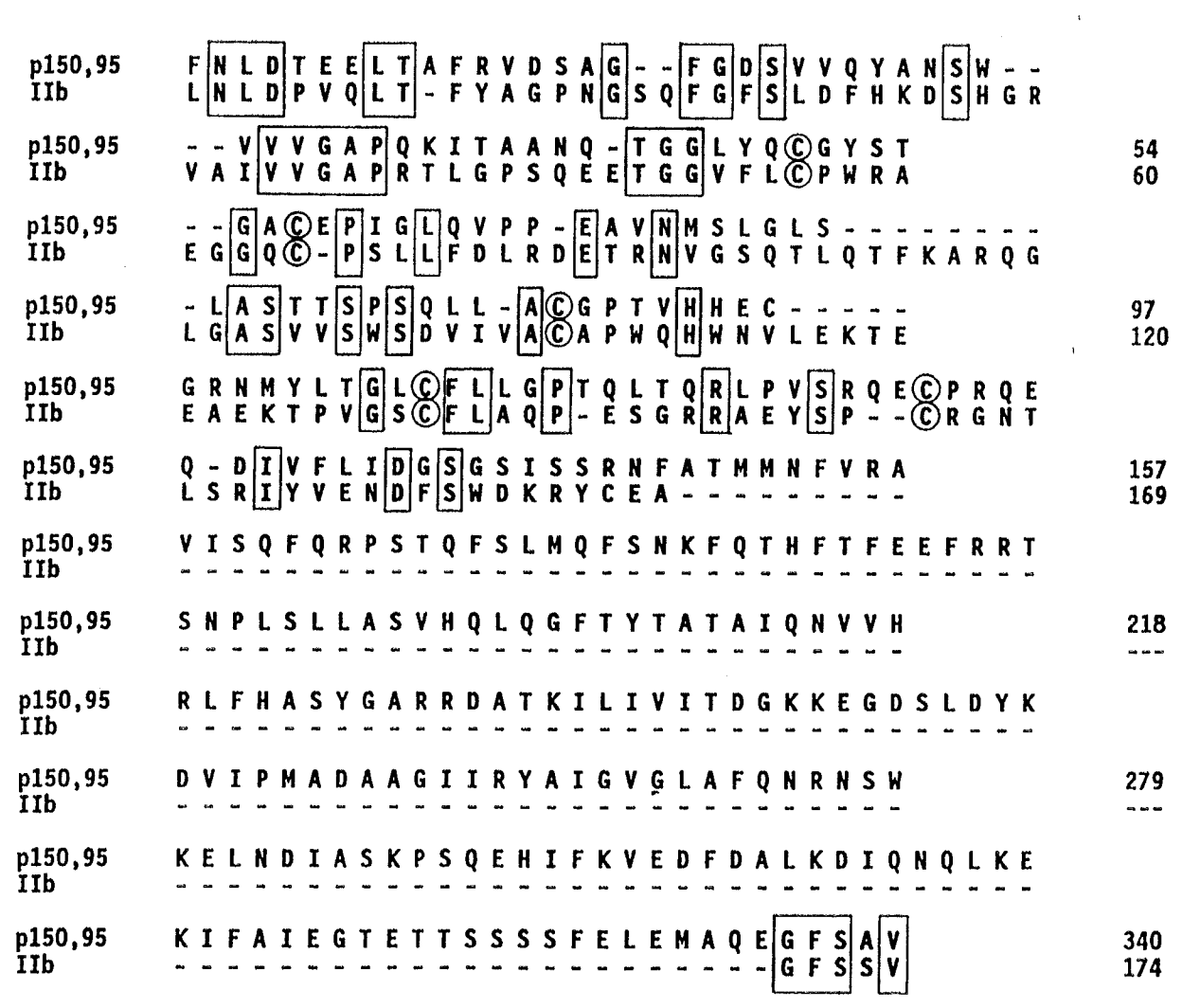
Figure 6B:
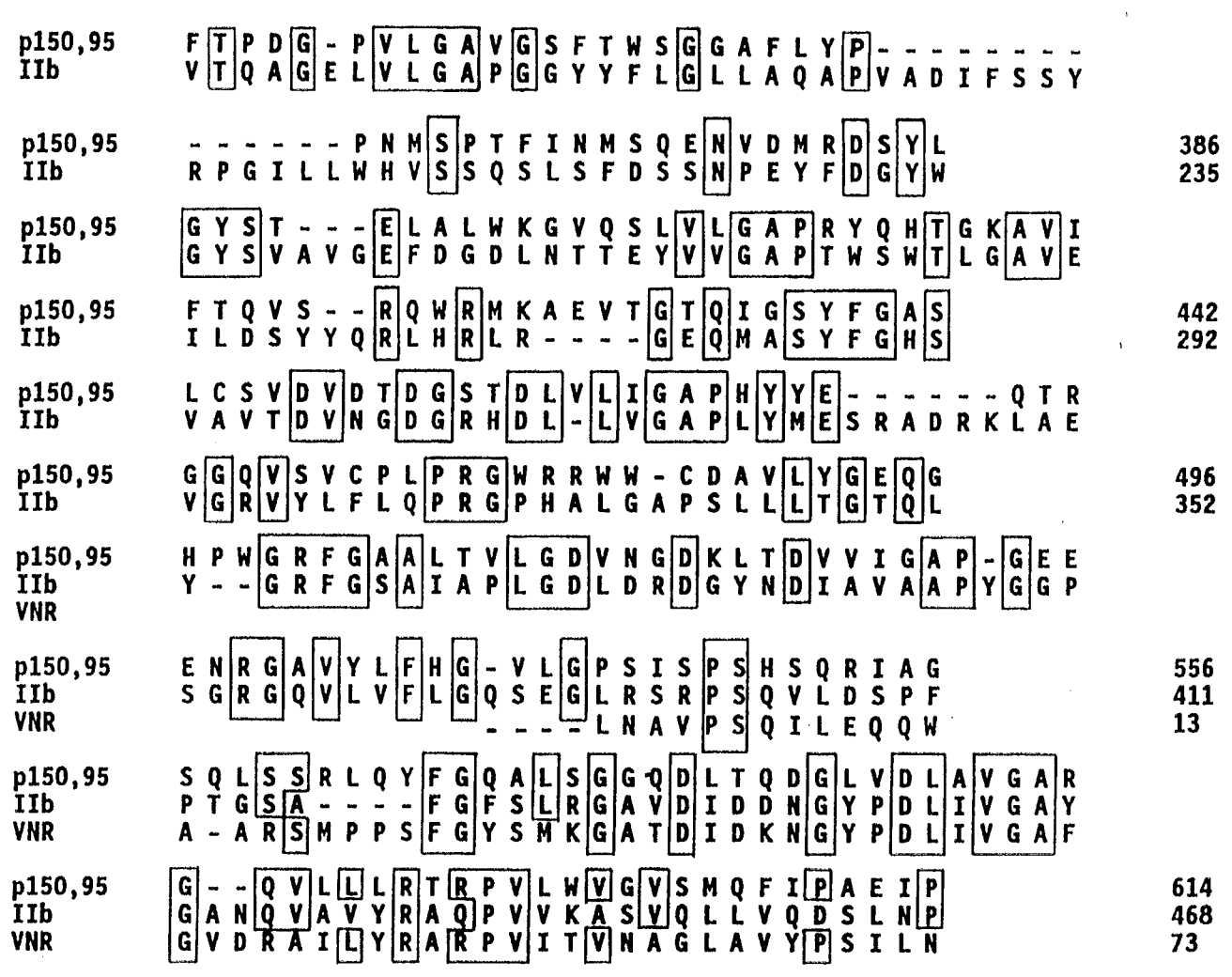
Figure 6C:
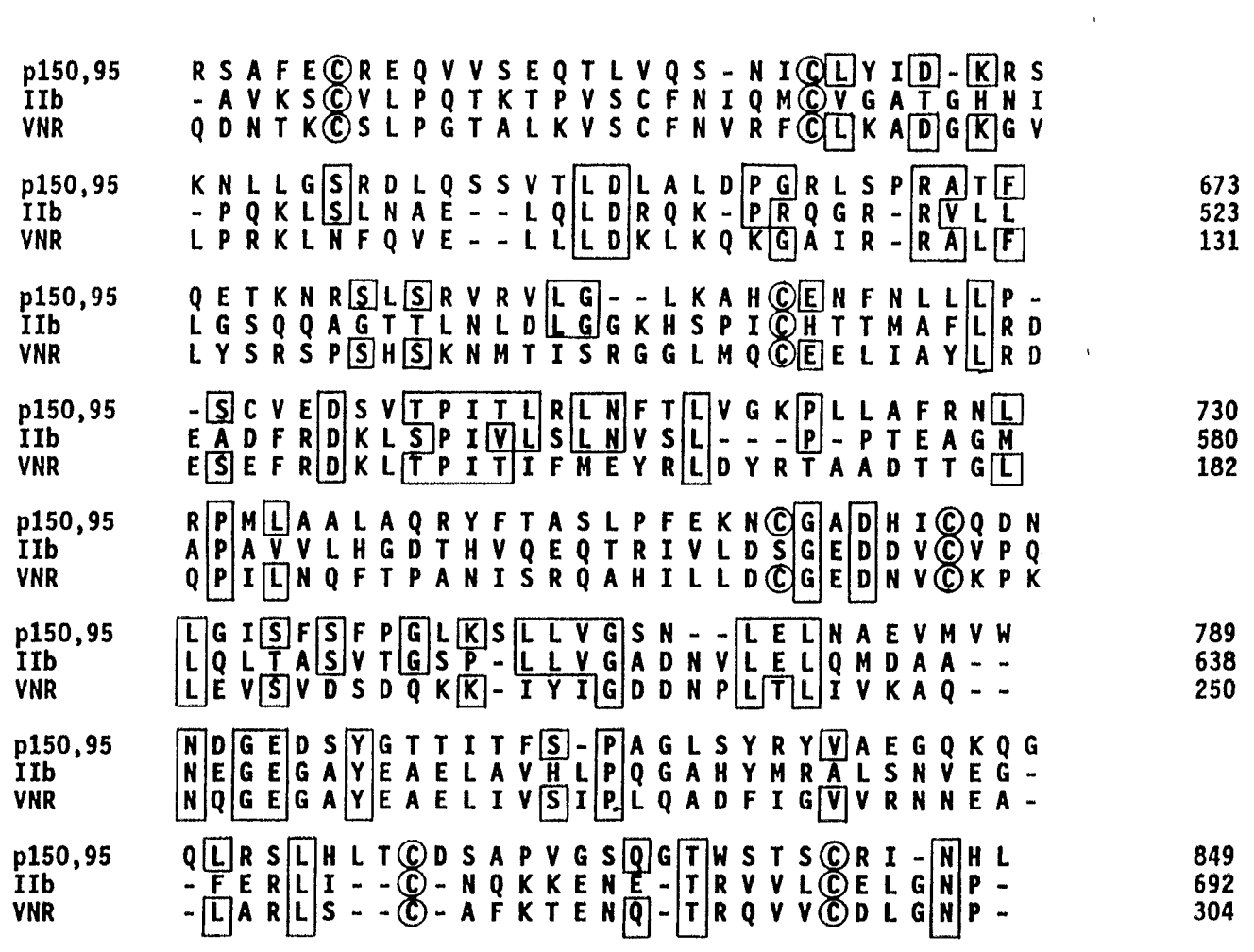
Figure 6D:
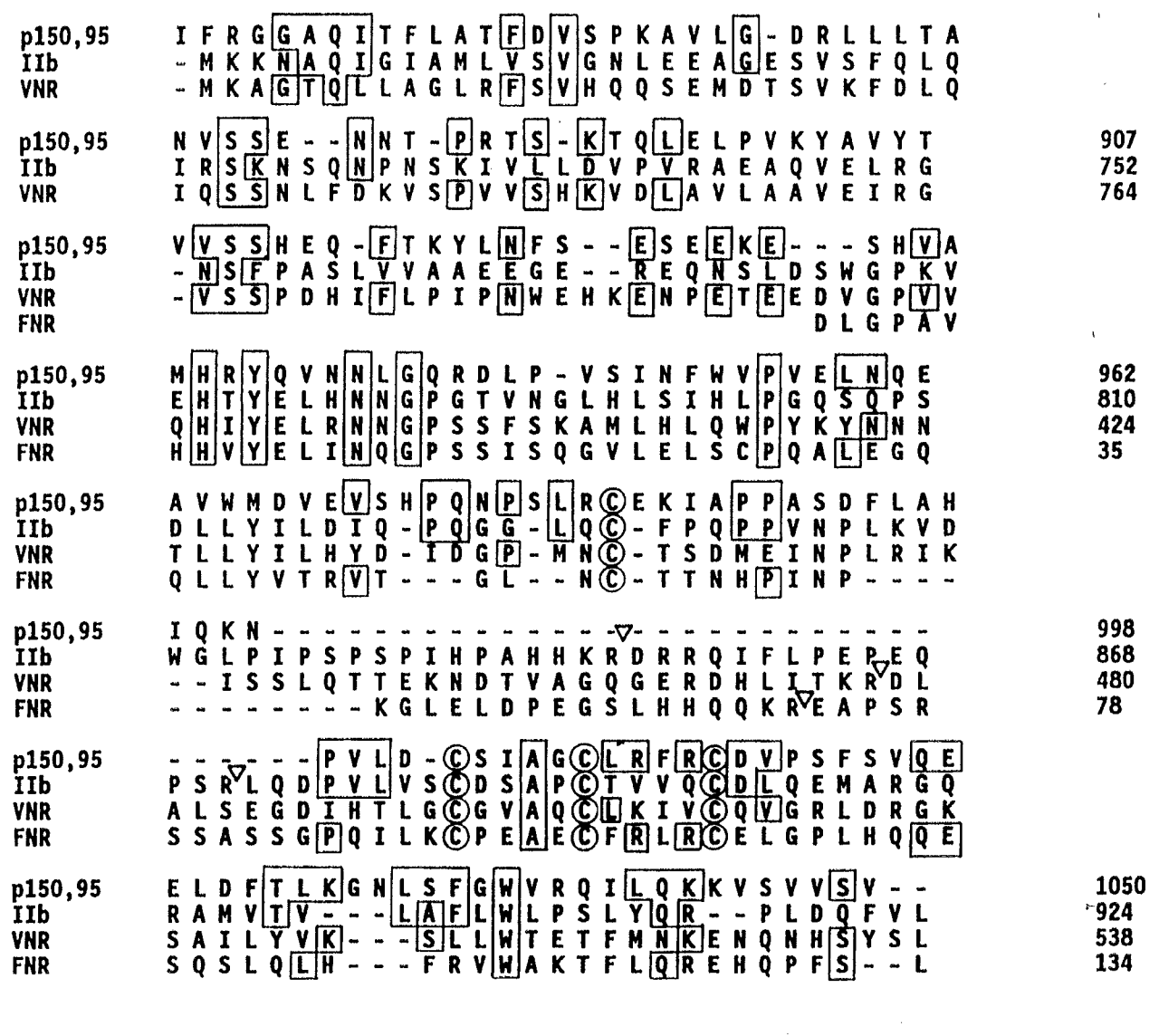

FIG. 6 compares the homology of the alpha chain of the p150,95 molecule to the alpha chains of the platelet glycoprotein IIb/IIIa, vitronectin receptor and fibronectin receptor. Identities between the 150,95 alpha-subunit and the other alpha-subunits are boxed, except for the cysteine residues which are circled. The cleavage sites for the RGD-receptor alpha-subunits are indicated by arrow heads.

DESCRIPTION OF THE PREFERRED EMBODIMENTS

Figure 1:
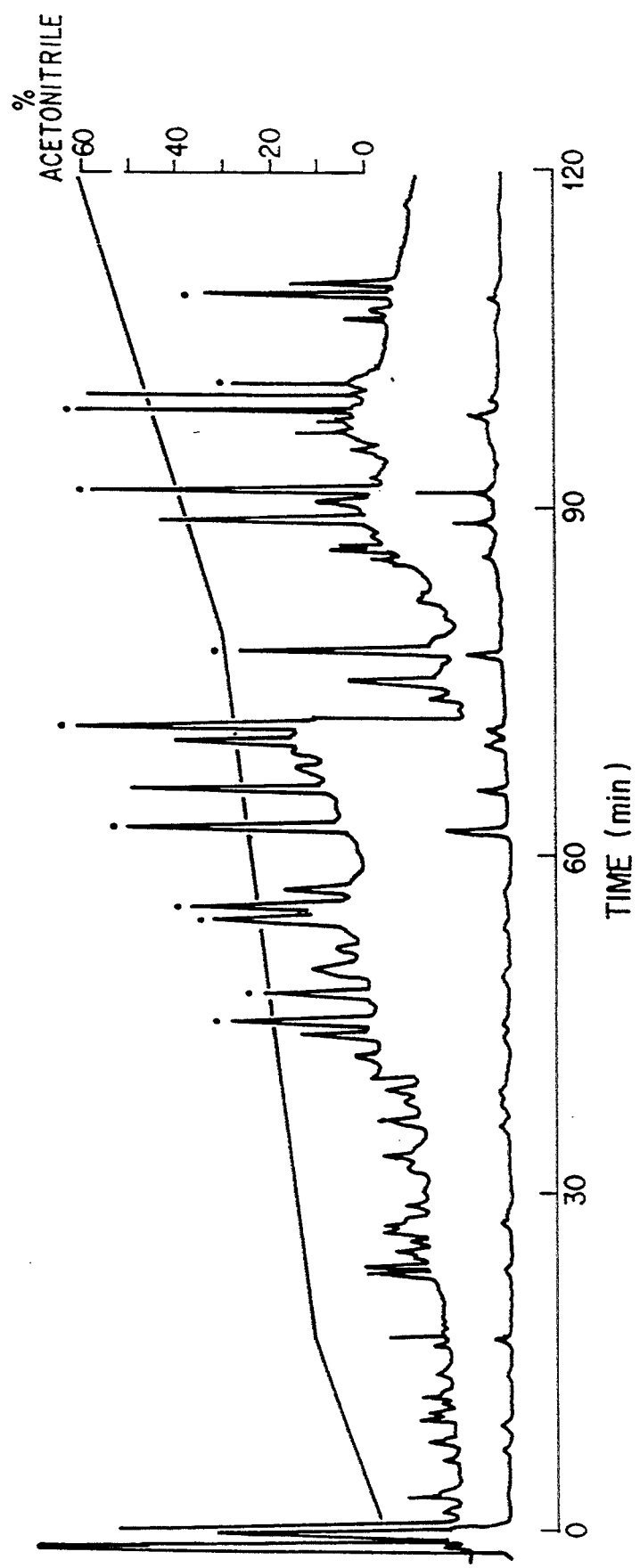
FIG. 1 shows a profile of the reverse-phase HPLC separation of the p150,95 alpha-subunit tryptic peptides. Elution was monitored by optical density at 280 nm (lower profile) and 214 nm (upper profile). The peptides indicated by a dot were subjected to protein microsequencing. The line across the profile indicates the percentage of acetonitrile.

I. The Nature of the Leukocyte Adhesion Proteins of the LFA-1 Family

The three leukocyte adhesion proteins Mac-1, p150,95, and LFA-1 differ in function and in expression on leukocyte subpopulations. Mac-1 and p150,95 are expressed on neutrophils, and monocytes (Springer, T.

A., et al., In: *Biochemistry of Macrophages* (CIBA Symposium 118); Pitman, London, pp. 102-126 (1986)). During differentiation of blood monocytes into tissue macrophages, expression of p150,95 is greatly increased and Mac-1 expression is decreased (Schwarting, R., et al., *Blood* 65:974-983 (1985); Hogg, N., et al., *Eur. J. Immunol.* 15:240-248 (1986)). p150,95 is also expressed on certain types of activated T and B lymphocytes, but is not expressed on these cells in the blood (Kaligaris-Cappio, F., et al., *Blood* 66:1035-1042 (1985); Miller, L. J., et. al., *J. Immunol.* 137:2891-2900 (1986); Keizer, G. D., et al., *J. Immunol.* 138:3130-3136 (1987)).

Mac-1 and p150,95 are expressed in an intracellular, vesicular compartment in circulating neutrophils and monocytes which is mobilized to the cell surface by inflammatory mediators (Todd, R. F., et al., *J. Clin. Invest.*, 74:1280-1290 (1984); Springer, T. A., et al., In: *Biochemistry of Macrophages* (CIBA Symposium 118), Pitman, London, pp. 102-126 (1986); Lanier, L. L., et al., *Eur. J. Immunol.* 15:713-718 (1985); Yancey, K. B., et al., *J. Immunol.* 135:465-470 (1985)). This mobilization correlates with increased adhesiveness (Anderson, D.C., et al., *Ann. Rev. Med.* 38:175-194 (1987)).

Monoclonal antibodies to Mac-1 or p150,95 inhibit neutrophil aggregation and adherence to endothelial cells, protein-coated surfaces, bacteria, protozoan parasites, and fungi (Harlan, J. M., et al., *Blood* 66:167-178 (1985); Springer, T. A., et al., In: *Biochemistry of Macrophages* (CIBA Symposium 118), Pitman, London, pp. 102-126 (1986); Dana, N., et al., *J. Immunol.* 137.:3259 (1986); Bullock, W. D., et al., *J. Exper. Med.* 165:195-210 (1987); Mosser, D. M., et al., *J. Immunol.* 135:2785-2789 (1985)).

Mac-1 is also a receptor for the complement component iC3b (Beller, D. I., et al., *J. Exper. Med.* 156:1000-1009 (1982)). Detergent-soluble Mac-1 and p150,95 have been shown to be able to bind to iC3b-Sepharose (Micklem, K. J., et al., *Biochem. J.* 231:233-236 (1985)).

LFA-1 is present on all leukocytes except a subset of macrophages. Monoclonal antibody blocking) studies have shown that LFA-1 is important in T-lymphocyte-mediated killing, T helper lymphocyte responses, natural killing, and antibody-dependent killing (Springer, T. A., et al., *Ann. Rev. Immunol.* 5:223-252 (1987)). Adhesion to the target cell is a step which is blocked by antibodies against LFA-1. Functional studies have suggested that LFA-1 interacts with several ligands, one of which is ICAM-1 (Rothlein, R., et al., *J. Immunol.* 137:1270-1274 (1986)).

Some cytotoxic T lymphocyte clones have been found to express similar quantities of p150,95 and LFA-1. Monoclonal antibodies to the LFA-1 and p150,95 alpha-subunits inhibit killing by such CTL clones to similar extents and are additive in their inhibitory effects (Keizer, G. D., et al., *J. Immunol.* 138:3130-3136 (1987)). Furthermore, antibodies to p150,95 alpha subunits have been shown to inhibit monocyte attachment to endothelium (Keizer, G. D., et al., *Eur. J. Immunol.* 17:1317-1322 (1987)).

II. Cloning of the p150,95 Alpha-Subunit

Any of a variety of methods may be used to clone the p150,95 alpha-subunit gene. One such method entails analyzing a shuttle vector library of cDNA inserts (derived from a p150,95 alpha-subunit expressing cell) for the presence of an insert which contains the p150,95 alpha-subunit gene. Such an analysis may be conducted by transfecting cells with the vector, and then assaying for p150,95 alpha-subunit expression. A preferred method for cloning the p150,95 alpha-subunit gene entails determining the amino acid sequence of the p150,95 alpha-subunit molecule. To accomplish this task, p150,95 alpha-subunit molecules are preferably purified from producer cells by monoclonal antibody affinity chromatography and isolated by preparative sodium dodecyl sulfate-polyacrylamide gel electrophoresis ("SDS-PAGE") and electroelution (Miller, L. J., et al., *J. Immunol.* 138:2381-2383 (1987), which reference herein is incorporated by reference). The alpha-subunit molecules are fragmented as with cyanogen bromide, or with proteases such as papain, chymotrypsin, or trypsin (Oike, Y., et al., *J. Biol. Chem.* 257:9751-9758 (1982); Liu, C., et .al., *Int. J. Pept. Protein Res.* 21:209-215 (1983)). Preferably, the alpha-subunit is proteolytically digested with trypsin. The resulting peptides are separated by reverse-phase HPLC and subjected to amino acid sequencing. To accomplish this task, the protein is, preferably, analyzed by automated sequenators. Although it is possible to determine the entire amino acid sequence of the p150,95 alpha-subunit, it is preferable to determine the sequence of peptide fragments of the molecule.

The sequence of amino acid residues in a peptide is designated herein either through the use of their commonly employed three-letter designations or by their single-letter designations. A listing of these three-letter and one-letter designations may be found in textbooks such as *Biochemistry*, Lehninger, A., Orth Publishers, New York, N.Y. (1970). When such a sequence is listed vertically, the amino terminal residue is intended to be at the top of the list, and the carboxy terminal residue of the peptide is intended to be at the bottom of the list. Similarly, when listed horizontally, the amino terminus is intended to be on the left end whereas the carboxy terminus is intended to be at the right end.

The residues of amino acids in a peptide may be separated by hyphens. Such hyphens are intended solely to facilitate the presentation of a sequence. As a purely illustrative example, the amino acid sequence designated:

—Gly—Ala—Ser—Phe— indicates that an Ala residue is linked to the carboxy group of Gly, and that a Set residue is linked to the carboxy group of the Ala residue and to the amino group of a Phe residue. The designation further indicates that the amino acid sequence contains the tetrapeptide Gly-Ala-Ser-Phe. The designation is not intended to limit the amino acid sequence to this one tetrapeptide, but is intended to include (1) the tetrapeptide having one or more amino acids linked to either its amino or carboxy end, (2) the tetrapeptide having one or more amino acid residues linked to both its amino and its carboxy ends, (3) the tetrapeptide having no additional amino acid residues.

Once one or more suitable peptide fragments have been sequenced, the DNA sequences capable of encoding them are examined. Because the genetic code is degenerate, more than one codon may be used to encode a particular amino acid (Watson, J. D., In: *Molecular Biology of the Gene,* 3rd Ed., W. A. Benjamin, Inc., Menlo Park, Calif. (1977), pp. 356-357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequences may be encoded by only a single oligonucleotide, frequently the amino acid sequence may be encoded by any of a set of similar oligonucleotides. Important, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

A suitable oligonucleotide, or set of oligonucleotides, which is capable of encoding a fragment of the p150,95 alpha-subunit gene (or which is complementary to such an oligonucleotide, or set of oligonucleotides) is identified (using the above-described procedure), synthesized, and hybridized by means well known in the art, against a DNA or, more preferably, a cDNA preparation derived from human cells which are capable of expressing the p150,95 alpha-subunit gene. Techniques of nucleic acid hybridization are disclosed by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, D.C. (1985)), which references are herein incorporated by reference. The source of DNA or cDNA used will preferably have been enriched for p150,95 alpha-subunit sequences. Such enrichment can most easily be obtained from cDNA obtained by extracting RNA from cells which produce high levels of the p150,95 alpha-subunit. An example of such a cell is a B lymphocyte from an individual suffering from hairy cell leukemia.

Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *Eur. Mol. Biol. Organ. J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

Using the genetic code (Watson, J. D., In: *Molecular Biology of the Gene,* 3rd Ed., W. A. Benjamin, Inc., Menlo Park, Calif. (1977)), one or more different oligonucleotides can be identified, each of which would be capable of encoding the p150,95 alpha-subunit tryptic peptides. The probability that a particular oligonucleotide will, in fact, constitute the actual p150,95 alpha-subunit-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the p150,95 alpha-subunit tryptic peptide sequences is identified.

The oligonucleotide, or set of oligonucleotides, containing the theoretical "most probable" sequence capable of encoding the p150,95 alpha-subunit fragments is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the p150,95 alpha-subunit gene (Maniatis, T., et al., *Molecular Cloning A Laboratory Manual,* Cold Spring Harbor Press, Cold Spring Harbor, N.Y. (1982).

Thus, in summary, the actual identification of p150,95 alpha-subunit peptide sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe to identify and isolate the p150,95 alpha-subunit gene.

Single stranded oligonucleotide molecules complementary to the "most probable" p150,95 alpha-subunit tryptic peptide encoding sequences were synthesized using procedures which are well known to those of ordinary skill in the art (Belagaje, R., et al., *J. Biol. Chem.* 254:5765–5780 (1979); Maniatis, T., et al., In: *Molecular Mechanisms in the Control Of Gene Expression,* Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers.

It is possible to clone the p150,95 alpha-subunit gene from eukaryotic DNA preparations suspected of containing this gene. To identify and clone the gene which encodes the p150,95 alpha-subunit protein, a DNA, or more preferably a cDNA, library is screened for its ability to hybridize with the oligonucleotide probes described above. Suitable DNA preparations (such as human genomic DNA) are enzymatically cleaved, or randomly sheared, and ligated into recombinant vectors. The ability of these recombinant vectors to hybridize to the above-described oligonucleotide probes is then measured. Procedures for hybridization are disclosed, for example, in Maniatis, T., *Molecular Cloning A Laboratory Manual,* Cold Spring Harbor Press, Cold Spring Harbor, N.Y. (1982) or in Hames, B. T., et al., *Nucleic Acid Hybridization a Practical Approach,* IRL Press, Oxford, England (1985). Vectors found capable of such hybridization are then analyzed to determine the extent and nature of the p150,95 alpha-subunit sequences which they contain. Based purely on statistical considerations, a gene such as that which encodes the p150,95 alpha-subunit molecule could be unambiguously identified (via hybridization screening) using an oligonucleotide probe having only 18 nucleotides.

The cloned p150,95 alpha-subunit gene, obtained through the method described above, may be operably linked to an expression vector, and introduced into prokaryotic or eukaryotic cells to produce the p150,95 alpha-subunit protein. Techniques for such manipulations are disclosed by Maniatis, T., et al., supra, and are well known in the art.

III. The Expression of the p150,95 Alpha-Subunit

The present invention derives, in part, from the discovery of the cDNA sequence which encodes the alpha-subunit of the p150,95 molecule. By operably linking this sequence (or a fragment of this sequence) to a functional promoter, it is possible to direct the expression of the alpha-subunit of p150,95 (or a functional derivative thereof) in a cell, or organism.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Regulatory regions in eukaryotic cells will in general include a promoter region sufficient to direct the initiation of RNA synthesis.

Two DNA sequences (such as a promoter region sequence and a p150,95 alpha-subunit-encoding sequence) are said to be operably linked if the nature of the linkage between the two DNA sequences does not (1) result in the introduction of a frame-shift mutation, (2) interfere with the ability of the promoter region sequence to direct the transcription of the p150,95 alpha-subunit-encoding sequence, or (3) interfere with the ability of the p150,95 alpha-subunit-encoding sequence to be transcribed by the promoter region sequence. Thus, a promoter region would be operably linked to a DNA sequence if the promoter were capable of effecting transcription of that DNA sequence.

The present invention encompasses the expression of the p150,95 alpha-subunit (or a functional derivative thereof) in either prokaryotic or eukaryotic cells. To express the p150,95 alpha-subunit (or a functional derivative thereof) in a prokaryotic cell (such as, for example, $E.\ coli$, $B.\ subtilis$, Pseudomonas, Streptomyces, etc.), it is necessary to operably link the p150,95 alpha-subunit-encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pPR325, etc. Examples of inducible prokaryotic promoters include the major right and left promoters of bacteriophage λ ($P_L$ and $P_R$), the trp, recA, lacZ, lacI, and gal promoters of $E.\ coli$, the α-amylase (Ulmanen, I., et al., $J.\ Bacteriol.$ 162:176–182 (1985)) and the σ-28-specific promoters of $B.\ subtilis$ (Gilman, M. Z., et al., $Gene$ 32:11–20 (1984)), the promoters of the bacteriophages of Bacillus (Gryczan, T. J., In: $The\ Molecular\ Biology\ of\ the\ Bacilli$, Academic Press, Inc., NY (1982)), and Streptomyces promoters (Ward, J. M., et al., $Mol.\ Gen.\ Genet.$ 203:468–478 (1986)). Prokaryotic promoters are reviewed by Glick, B. R., ($J.\ Ind.\ Microbiol.$ 1:277–282 (1987)); Cenatiempo, Y. ($Biochimie$ 68:505–516 (1986)); and Gottesman, S. ($Ann.\ Rev.\ Genet.$ 18:415–442 (1984)).

Proper expression in a prokaryotic cell requires the presence of a ribosome binding site upstream of the gene-encoding sequence. Such ribosome binding sites are disclosed, for example, by Gold, L., et al. ($Ann.\ Rev.\ Microbiol.$ 35:365–404 (1981)).

If expression is desired in a eukarotic cell, such as yeast, fungi, mammalian cells, or plant cells, then it shall be necessary to employ a promoter capable of directing transcription in such a eukaryotic host. Preferred eukaryotic promoters include the promoter of the mouse metallothionein I gene (Hamer, D., eta)., $J.\ Mol.\ Appl.\ Gen.$ 1:273–288 (1982)); the TK promoter of Herpes virus (McKnight, S., $Cell$ 31:355–365 (1982)); the SV40 early promoter (Benoist, C., et al., $Nature\ (London)$ 290:304–310 (1981)); the yeast gal4 gene promoter (Johnston, S. A., et al., $Proc.\ Natl.\ Acad.\ Sci.\ (USA)$ 79:6971–6975 (1982); Silver, P. A., et al., $Proc.\ Natl.\ Acad.\ Sci.\ (USA)$ 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the p150,95 alpha-subunit (or a functional derivative thereof) does not contain any intervening codons which are capable of encoding a methionine (i.e., AUG). The presence of such codons results either in a formation of a fusion protein (if the AUG codon is in the same reading frame as the p150,95 encoding DNA sequence) or a frame-shift mutation (if the AUG codon is not in the same reading frame as the p150,95 encoding sequence).

A DNA sequence which encodes the p150,95 protein (or a functional derivative thereof) when operably linked to a functional promoter is preferably introduced into a recipient cell by any of a variety of suitable means: transformation, transfection, conjugation, protoplast fusion, electroporation, etc.

The p150,95 alpha-subunit-encoding sequence and an operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the p150,95 alpha-subunit polypeptide may occur through the transient expression of the introduced sequence. Alternatively, permanent expression may occur through the integration of the introduced sequence into the host chromosome.

Preferably, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in $E.\ coli$ (such as, for example, pBR322, ColE1, pSC101, pACYC184, πVX. Such plasmids are, for example, disclosed by Maniatis, T., et al. (In: $Molecular\ Cloning$,

*A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, NY (1982), pp. 307–329). Suitable Streptomyces plasmids include pIJ101 (Kendall, K. J., et al., *J. Bacteriol.* 169:4177–4183 (1987)), and streptomyces bacteriophages such as φC31 (Chater, K. F., et al., In: *Sixth International Symposium on Actinomyceteles Biology*, Akademiai Kaido, Budapest, Hungary (1986), pp. 45–54). Pseudomonas plasmids are reviewed by John, J. F., et al. (*Rev. Infect Dis.* 8:693–704 (1986)), and Izaki, K. (*Jpn. J. Bacteriol.* 33:729–742 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise, Vol. 3, Gene Expression*, Academic Press, NY, pp. 563–608 (1980)).

IV. Uses of the p150,95 Alpha-Subunit, or Fragments Thereof

The present invention provides the nucleic acid and protein sequences of the alpha-subunit of the p150,95 receptor molecule. This discovery permits the use of recombinant DNA technology to produce the p150,95 alpha-subunit molecule. As discussed further below, one embodiment of the present invention pertains to the use of the alpha-subunit of the p150,95 molecule by itself, as an anti-inflammatory agent. In a preferred embodiment, the alpha-subunit of the p150,95 molecule will be used in combination with its beta-subunit. Such a combination maybe produced using a variety of methods. For example, the beta-subunit of p150,95 may be produced separately from the p150,95 alpha-subunit, and the two molecules may then be mixed together. It is, however, preferable to produce both the alpha and beta-subunits of p150,95 in the same host cell in order to facilitate their self-assembly into the p150,95 heterodimer receptor molecule. The beta-subunit of p150,95 (which is common to LFA-1, and Mac-1) may be produced either by chemical synthesis, or by recombinant DNA techniques (Kishimoto, T. K., et al., *Cell* 48:681–690 (1987)). The cloning of the beta-subunit of p150,95 is further disclosed in commonly assigned, copending U.S. patent application Ser. No. 019,440, tiled on Feb. 26, 1989, now abandoned, which application is herein incorporated by reference.

One aspect of the present invention relates to the discovery of the nucleic acid and protein sequences of the alpha-subunit of the p150,95 receptor molecule. This discovery permits the use of recombinant DNA technology to produce functional derivatives of the p150,95 alpha-subunit which may function as antagonists of cellular adhesion. As used herein, an "antagonist of cellular adhesion" is meant to refer to any molecule capable of inhibiting the process of cell-cell or cell-substrate adhesion. It is possible to determine whether a particular compound is an antagonist by performing an assay of monocyte adhesion to endothelial cells. Suitable assays of cellular adhesion are disclosed, for example, (Keizer, G. D., et al. *Eur. J. Immunol.* 17:1317–1322 (1987)) which reference is herein incorporated by reference. Antagonists of cellular adhesion may be employed as anti-inflammatory agents.

As used herein, a "functional derivative" of the alpha-subunit of p150,95 is a compound which possesses a biological activity (either functional or structural) that is substantially similar to a biological activity of the alpha subunit of p150,95. Examples of biological activities include the ability to bind to the β-subunit of the LFA family of glycoproteins, and the ability to competitively inhibit the binding of anti-alpha-subunit p150,95 antibody to the p150,95 alpha-subunit. A molecule is said to be "substantially similar" to another molecule if both molecules have substantially similar structures or if both molecules possess a similar biological activity. The "functional derivatives" of the alpha-subunit of p150,95 include both "fragments" and "variants" of the p150,95 alpha-subunit. The term "fragment of the alpha-subunit of p150,95" is meant to refer to any polypeptide subset of that molecule. The term "variant of the alpha-subunit of p150,95" is meant to refer to a molecule substantially similar in structure to either the entire molecule, or to a fragment thereof provided that the "variant" has at least one biological activity that is either similar to an activity of the alpha-subunit of p150,95 or inhibitory to an activity of p150,95. Thus, provided that a molecule possesses at least one biological activity that is either similar to an activity of p150,95 or inhibitory to such an activity, it is considered a "variant" of the alpha-subunit p150,95, as that term is used herein, even if one of the molecules contains one or more amino acids not found in the other, or if the sequences of amino acid residues in the two molecules are not identical. Thus, for example, a compound lacking (or containing) one or more amino acid residues found (or not found) in the alpha-subunit of p150,95 would be considered to be a variant of the alpha-subunit of p150,95 if that compound possessed a biological activity similar to (or inhibitory to) a biological activity of the alpha-subunit of p150,95. The term "biological activity" is intended to encompass "catalytic" as well as "structural" activity (i.e., the capacity to bind to another molecule, such as the beta-subunit of p150,95, or anti-alpha-subunit p150,95 antibody), etc.

The present invention provides a method for producing functional derivatives of the alpha-subunit of the p150,95 molecule. To obtain such derivatives, it is necessary only to mutagenize a DNA, RNA, or (more preferably) the cDNA sequence which encodes the p150,95 alpha-subunit. Mutagenesis can either be random, or site specific. Further, mutagenesis may either be spontaneous or induced using chemical, radioactive, or recombinant techniques.

Chemical mutagens include base analogs (such as, for example, 5-bromouracil, or 2-aminopurine); deaminating agents (such as, for example, nitrous acid, hydroxylamine, etc.); alkylating agents (such as, for example, methyl methanesulphonate, nitrosaguanidine, etc.); or intercolating agents (such as, for example, acridine orange, ethidium bromide, psoralen, etc.). Radiation-induced mutation can be caused by agents such as ultraviolet light, gamma, X ray, etc. Techniques for mutagenizing nucleic acid molecules may be found in Miller, J. H. (In: *Experiments in Molecular Biology*, Cold Spring Harbor Laboratory, Cold Spring Harbor, N.Y. (1972)), and Silhavy, T. J., et al. (In: *Experiments with Gene Fusions*, Cold Spring Harbor Laboratory, Cold Spring Harbor, N.Y. (1984)).

Site-specific mutagenesis may be employed to produce specific mutations as desired sites of the nucleic acid encoding the p150,95 alpha-subunit. In brief, such procedures generally entail the synthesis of a synthetic oligonucleotide having a desired and defined DNA sequence. Methods for synthesizing such oligonucleotides are disclosed by Itakura, K., et al. (*Ann. Rev. Biochem.* 53:323–356 (1984)). A nucleic acid molecule which encodes the p150,95 alpha-subunit protein, or a functional derivative thereof, is generally subcloned onto a double-stranded vector such as M13, φX174, etc., whose single strands may be separated one from another. A single strand of the vector is then incubated in the presence of the synthetic oligonucleotide. Since the DNA of the oligonucleotide is controllably defined, it is possible to construct an oligonucleotide capable of base pairing with any region of the p150,95 alpha-subunit-encoding nucleic acid. Once base pairing has occurred between the oligonucleotide and the single-stranded plasmid, it is possible to extend the oligonucleotide using DNA polymerase to create a double-stranded DNA molecule which may then be sealed by DNA ligase. When this double-stranded DNA molecule is introduced into a cell, semi-conservative DNA replication will result in the production of progeny molecules in which the DNA sequence of the oligonucleotide fragment has been incorporated into the p150,95 alpha-subunit-encoding sequences.

Thus, if one desired to introduce a point mutation, and exogenous DNA sequence into a specific site in the p150,95-encoding sequence, or to create a deletion of nucleotides normally present in such a sequence, one would design an oligonucleotide fragment which contained (or lacked) the mutation or sequence, and then pursue the above-described procedure. In order to introduce such a mutation or exogenous DNA sequence into a particular region of the p150,95 alpha-subunit-encoding nucleic acid, it is necessary to surround the mutation or the exogenous DNA sequence with flanking DNA sequences that are complementary to the DNA sequence of the region whose mutagenesis is desired. (Jenkins, F., et al., *Bioessays* 5:244–247 (1986); Doerfler, W., *Anger. Chem. Int. Ed. Engl.* 23:919–931 (1984); Kaina, B., *Biol. Zentralbl.* 99:513–531 (1980); Kunkel, *Proc. Natl. Acad. Sci. (USA)* 82:488–492 (1985); Nisbet, I. T., et al., *Gene Anal. Tech.* 2:23–29 (1985); Hines, J. C., et al., *Gene* 11::207–218 (1980); Messing, J., et al., *Nucl. Acid. Res.* 9:309 (1981)).

Mutations can also be produced through the application of recombinant DNA technology. For example, the nucleotide sequence of a nucleic acid molecule which encodes the p150,95 alpha-subunit can be scanned to identify oligonucleotide sites which are recognizable by restriction endonucleases. Such endonucleases can then be used to specifically cleave the nucleic acid sequence at a recognized site. By using a restriction endonuclease that recognizes (and cleaves at) two positions in the p150,95-encoding sequence, it is possible to excise a fragment of the p150-95-encoding sequence. Alternatively, it is possible to use two different endonucleases for this purpose. By incubating the cleaved molecules in the presence of DNA ligase, it is possible to reseal the p150,95 alpha-subunit-encoding sequences to form a single sequence (which lacks the excised fragment). If no appropriate restriction endonuclease recognition sites exist in the p150,95 alpha-subunit-encoding sequences, then such sites may be introduced into the sequences by the site-specific mutagenesis procedure described above.

Mutations may alternatively be introduced by cleaving the p150,95 alpha-subunit-encoding sequence and "nibbling" the free termini with an exonuclease. By such treatment it is possible to introduce not only deletions, but frame-shift and other types of mutations. This technique is, moreover, capable of introducing novel restriction endonuclease sites into the p150,95 alpha-subunit-encoding sequence. Methods for using restriction endonucleases, DNA ligases, and exonucleases are disclosed, for example, by Maniatis, T., et al. (In: *Molecular Cloning, A Laboratory Manual*, Cold Spring Harbor Laboratory, Cold Spring Harbor, N.Y. (1982)).

Recombinant DNA techniques may also be used to produce fusion proteins composed of the p150,95 alpha-subunit protein (or a functional derivative thereof) and a novel polypeptide. This novel polypeptide is not limited to any particular polypeptide and may comprise either a single amino acid or any set or permutation of amino acids. Such fusion molecules may be produced by ligating a DNA sequence which encodes the novel polypeptide to a DNA sequence which encodes the p150,95 alpha-subunit (or a functional derivative thereof), in a manner which does not introduce a frame-shift mutation. Examples of preferred polypeptides which may be fused to the p150,95 alpha-subunit gene (or a functional derivative thereof) include eukaryotic or prokaryotic signal sequences (Gilbert, W., et al., U.S. Pat. No. 4,411,994; Kasadaban, M., et al., *Proc. Natl. Acad. Sci. (USA)* 76:4530–4533 (1979)), or polypeptides which extend (or diminish) the stability, biological half-life, or potency of the p150,95 alpha-subunit (or a functional derivative thereof). An excellent review of the methodology of gene fusions is provided by Silhavy, T. J., et al. (In: *Experiments with Gene Fusions*, Cold Spring Harbor Laboratory, Cold Spring Harbor, N.Y. (1984)).

Antibodies (especially monoclonal antibodies) may be elicited in response to immunization with fragments of the p150,95 alpha-subunit. Such antibodies can be used to prevent the binding of some leukocytes to endothelial cells, and thus may be employed as anti-inflammatory agents.

Using the methods described above, fragments of the p150,95 alpha-subunit may be prepared and assayed to determine whether they are antagonists of cellular adhesion. Fragments found to be antagonists of cellular adhesion may be employed as anti-inflammatory agents in accordance with the present invention.

The present invention derives in part from the discovery that granulocyte substrate adhesion and monocyte-endothelial cell adherence results from interactions involving the p150,95 receptor. Since cellular adhesion is required in order that leukocytes may migrate to sites of inflammation and/or carry out various effector functions contributing to inflammation, agents which inhibit cellular adhesion will attenuate or prevent inflammation. The p150,95 receptor molecule is present on the surface of monocyte cells. The adhesion of monocytes to plastic surfaces, or to monolayers of endothelial cells, is mediated by p150,95. In addition, the ability of monocytes to phagocytose foreign material has been found to be mediated by the p150,95 receptor. The receptor has also been implicated as having a role in chemokinesis, and chemotaxis of monocytes.

Agents which interfere with the capacity of the p150,95 receptor molecule to bind to its natural binding ligand are thus capable of impairing all of the above-described p150,95-dependent functions. Hence, these agents may serve as anti-inflammatory agents in accordance with the present invention. Such agents include the p150,95 alpha-subunit, p150,95 (alpha and beta-subunits), and antibody capable of binding to the p150,95 alpha-subunit, or to fragments of that subunit. All of such agents may be used in accordance with the present invention. The anti-inflammatory agents of the present invention are capable of treating inflammation caused by a reaction of either the specific or the non-specific defense system.

A "non-specific defense system reaction" is a response mediated by leukocyte cells incapable of immunological memory. Such cells include lymphocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; cytokine-induced toxicity and asthma.

As used herein, the term "specific defense system" is intended to refer to that component of the immune system that reacts to the presence of specific antigens. Such cells include lymphocytes and macrophages. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases, delayed-type hypersensitivity response mediated by T-cells (as seen, for example, in individuals who test "positive" in the Mantaux test), etc. The ability of p150,95 alpha-subunit and its functional derivatives to antagonize such inflammatory reactions provides the basis for their therapeutic use in the treatment of chronic inflammatory diseases and autoimmune diseases such as lupus erythemotosus, autoimmune thyroiditis, experimental allergic encephalomyelitis (EAE), multiple sclerosis, some forms of diabetes, Reynaud's syndrome, rheumatoid arthritis, etc.

Since p150,95 is expressed on cells which are capable of binding to endothelial tissue, the administration of the p150,95 alpha-subunit, or p150,95 (alpha and beta-subunits) to a patient provides a means for imaging or visualizing endothelial tissue. Moreover, this procedure provides diagnostic information concerning the quantity and distribution of the binding ligands of the p150,95 receptor molecule which are present on the visualized tissue. In such a use, the p150,95 alpha-subunits (or p150,95 alpha beta receptor molecules) are detectably labeled, through the use of radioisotopes, affinity labels (such as biotin, avidin, etc.) fluorescent labels, paramagnetic atoms, etc. Procedures for accomplishing such labeling are well known to the art. The antibodies (or fragments thereof) may be detectably labeled through the use of radioisotopes, enzyme labels, fluorescent labels, paramagnetic labels, electron-dense labels, toxin labels, etc. Preferred toxin labels include the diphtheria toxin, ricin, and cholera toxins. The administration of such labeled molecules into an individual will identify sites of inflammation. Such detectable labels can also be used to assay the status of a patient's immune system. Clinical application of antibodies in diagnostic imaging are reviewed by Grossman, H. B., *Urol. Clin. North Amer.* 13:465–474 (1986)), Unger, E. C. et al., *Invest. Radiol.* 20:693–700 (1985)), and Khaw, B. A. et al., *Science* 209:295–297 (1980)).

The ability of monocytes to migrate spontaneously to sites of inflammation is dependent upon p150,95 (Keizer, G. D., et al., *Eur. J. Immunol.* 17:1317–1322 (1987)). Such migration may be inhibited by administrating p150,95 alpha-subunits, or p150,95 (alpha and beta subunit) to a patient.

Similarly, the ability of monocytoid cells to adhere to endothelial cells, and the ability of monocytoid cells to undergo chemotaxis, chemokinesis, or phagocytosis has been found to be dependent upon p150,95 (Keizer, G. D., et al., *Eur. J. Immunol.* 17:1317–1322 (1987)). Any of the anti-inflammatory agents of the present invention maybe employed to inhibit such activites.

ICAMs (such as ICAM-1) are recognized by certain human viruses (particularly rhinoviruses of the major type (which bind to ICAM-1). These viruses bind to human cells by virtue of this recognition, and thereby mediate viral infection. Thus, a central step in the etiology of viral disease is the interaction between these cellular receptors and the virus.

Agents which suppress, compete with, or inhibit the ability of a virus to bind to an ICAM molecule thus have use in the treatment of viral (and particularly rhinoviral) infection.

One aspect of the present invention thus concerns the ability of the alpha-subunit of p150,95 and its functional derivatives to interact with ICAM-1 and to thereby either prevent cell-viral attachment and viral infection, or to attenuate or diminish the severity or duration of such infection.

Of particular interest to the present invention are functional derivatives of the alpha-subunit of p150,95 such as solubilized forms of the alpha-subunit of p150,95, fragments of the alpha-subunit of p150,95, etc. Such agents are preferably provided to a recipient patient as a heterodimer containing the molecule in association with a molecule of the beta-subunit of the CD-18 family. The above-described goal of treating viral infection may be accomplished with a single agent or with a combination of more than one agents.

For the purpose of treating viral infection, the above-described agent(s) of the present invention is to be provided to a recipient patient (for example, by intranasal means) at a dosage sufficient to permit the agent(s) to suppress, compete with, or inhibit the ability of a virus to bind to an ICAM molecule. Such a dosage shall, in general, be (for each agent provided) from 0.01 pg/kg patient weight to 1 mg/kg patient weight, although greater or lesser amounts can be employed.

For the purpose of treating viral infection, the administration of such agent(s) may be provided either "prophylactically" or "therapeutically." When provided prophylactically, the agent(s) are provided in advance of (i.e. prior to, at, or shortly after) the time of infection but in advance of any symptoms of viral infection. The prophylactic administration of the agent(s) serves to prevent or attenuate any subsequent infection. When provided therapeutically, the agent(s) are provided at (or shortly after) the onset of a symptom of actual viral infection (such as, for example, the appearance of virally induced nasal congestion, etc. or the detection of virus in bodily fluids, or the detection of antibodies, directed against the virus, in the serum of an infected patient, etc). The therapeutic administration of the agent(s) serves to attenuate any actual infection, and thus lessen its severity or duration.

V. Administration of the p150,95 Alpha-Subunit

The therapeutic effects of p150,95 alpha-subunit may be obtained by providing to a patient the p150,95 receptor molecule ($\alpha$ and $\beta$ subunits), the entire p150,95 alpha-subunit molecule, or any therapeutically active functional derivative thereof. These molecules may be obtained either synthetically, or through the use of recombinant DNA technology. Fragments of the p150,95 receptor or its alpha-subunit may additionally be obtained by proteolysis. The therapeutic advantages of these molecules may be augmented through the use of functional derivatives which possess additional amino acid residues added to enhance coupling to carrier or to enhance activity. The scope of the present invention is further intended to include functional derivatives which lack certain amino acid residues, or which contain altered amino acid residues, so long as such derivatives exhibit the capacity to enhance or inhibit cellular adhesion.

The molecules of the present invention are said to be "substantially free of natural contaminants" if preparations which contain them are substantially free of materials with which these products are normally and naturally found.

In providing a patient with the therapeutic molecules of the present invention, the dosage of administered agent will vary depending upon such factors as the patient's age, weight, height, sex, general medical condition, previous medical history, etc. In general, it is desirable to provide the recipient with a dosage of p150,95 alpha-subunit (or a functional derivative thereof) which is in the range of from about 1 pg/kg to 10 mg/kg (body weight of patient), although a lower or higher dosage may be administered.

The molecules of the present invention may be administered to patients intravenously, intramuscularly, subcutaneously, enterally, or parenterally. Administration may be by continuous infusion, or by single or multiple boluses.

The anti-inflammatory agents of the present invention are intended to be provided to recipient subjects in an amount sufficient to suppress inflammation. An amount is said to be sufficient to suppress inflammation if the dosage, route of administration, etc. of the agent are sufficient to attenuate or prevent inflammation. The anti-inflammatory agents of the present invention may be provided either prior to the onset of inflammation (so as to suppress the anticipated inflammation) or after the initiation of inflammation.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient. The molecules of the present invention can be formulated according to known methods to prepare pharmaceutically acceptable compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed.), Osol, A., ed., Mack, Easton, Pa. (1980). In order to form a pharmaceutically effective composition suitable for effective administration, such compositions will contain a therapeutically effective amount of p150,95 alpha-subunit, or its fragments or functional derivatives, together with a suitable amount of carrier vehicle.

Additional pharmaceutical methods may be employed to control the duration of action. Controlled release preparations may be achieved through the use of polymers to complex or absorb p150,95 alpha-subunit or its fragments or functional derivatives. The controlled delivery may be exercised by selecting appropriate macromolecules (for example, polyesters, polyamino acids, polyvinyl, pyrrolidone, ethylene vinylacetate, methylcellulose, carboxymethylcellulose, or protamine sulfate) and the concentration of macromolecules as well as the methods of incorporation in order to control release. Another possible method to control the duration of action by controlled release preparations is to incorporate p150,95 alpha-subunit molecules, their fragments, or their functional derivatives, into particles of a polymeric material such as polyesters, polyamino acids, hydrogels, poly(lactic acid), or ethylene vinylacetate copolymers. Alternatively, instead of incorporating these agents into polymeric particles, it is possible to entrap these molecules in microcapsules prepared, for example, by coacervation techniques or by interfacial polymerization, for example, hydroxymethyl cellulose or gelatin-microcapsules and poly(methylmethacrylate) microcapsules, respectively, or in colloidal drug delivery systems, for example, liposomes, albumin microspheres, microemulsions, nanoparticles, and nanocapsules in macroemulsions. Such techniques are disclosed in Remington's Pharmaceutical Sciences (1980).

Having now generally described the invention, the same will be more readily understood through reference to the following examples which are provided by way of illustration, and are not intended to be limiting of the present invention, unless specified.

EXAMPLE 1

Cloning of the p150,95 Alpha-Subunit Gene p150,95 is absent from normal B lymphocytes but is expressed in high levels in hairy cell leukemia, a B cell neoplasm in which the leukemia cells home to the spleen. The p150,95 molecule was purified from hairy cell leukemia spleens by monoclonal antibody affinity chromatography using the method of Miller, L. J., et al. (*J. Immunol.* 137:2891–2900 (1987)). The a subunit was isolated by preparative SDS-PAGE and electroelution (Hunkapiller, M. W., et al., *Met. Enzymol.* 91:227–336 (1983)) (FIG. 1). A total of 214 residues were determined from thirteen peptides. The peptide sequences are shown in Table 1 (residues of lower confidence are shown in parentheses). Regions of peptides #90a and #114 having lowest codon redundancy (Table 1, underlined) were chosen to design single sequence, codon usage preference oligonucleotide probes of 46 and 49 nucleotides, respectively (Lathe, R., et al., *J. Molec. Biol.* 183:1–12 (1985)).

Based on the finding that stimulation with PMA (phorbol myristate acetate) for 3 days induces high levels of p150,95 expression in the myelomonocytic cell line HL-60 (Miller et al., *J. Immunol.* 137:2891–2900 (1986)), PMA-stimulated HL-60 cell poly(A)+ mRNA was used as a template for cDNA synthesis using the method of Gubler, U., et al. (*Gene* 25:263–269 (1983)).

Total RNA was prepared from PMA-differentiated HL-60 cells as described by Chirgwin et al. (*Biochem.* 18:5294–5299 (1979)) and poly(A)+-RNA isolated by oligo-d(T) chromatography (Aviv, H., et al., *Proc. Natl. Acad. Sci.* 69:1408–1412 (1972)). 10 μg of poly(A)+-RNA was used to construct a cDNA library following the method of Gubler, U., et al., (*Gene* 25:263–269 (1983)).

Double-stranded cDNA larger than 2 kb was size selected by agarose gel electrophoresis, ligated to Eco RI linkers and cloned into λ gt10. Synthesis of the cDNA first strand was carried out using oligo-d(T) (Pharmacia) and reverse transcriptase (Life Sciences). Double-stranded cDNA synthesis was completed with DNA polymerase I (New England Biolabs), ribonuclease H (Boehringer Mannheim) and *E. coli* DNA ligase (New England Biolabs). Following the blunting and methylation reactions, phosphorylated Eco RI linkers (New England Biolabs) were ligated to the dscDNA. After RI digestion, linkers were removed in a 5 ml Sepharose CL 4B column (Pharmacia) and the first two thirds of the dsCDNA peak recovered. To select for members of the library having long inserts, the dscDNA was size-fractionated on a 0.8% low melting point agarose gel and the dscDNA between 2 and 7 kb was recovered by electroelution onto NA-45 paper (Schleicher & Schuell) and ligated into Eco RI-digested λ gt10. 3.2×10⁶ primary recombinants were obtained after packaging and plating on *E. coli* C600 hfl.

5×10⁵ primary recombinants were plated on *E. coli* C600 hfl at 25,000 plaques per 150 mm plate. Plaques were amplified in situ on duplicate nitrocellulose filters (Woo, S. L. C., *Met. Enzymol.* 68:389–395 (1979)), processed (Benton, W. D., et al , *Science* 196:180–182 (1977)) and prehybridized overnight at 37° C. in 6 X SSC, 1 X Denhardt's, 0.5% SDS, 0.05% Pi/PPi and 100 g/ml of tRNA. Hybridization was carried out at 37° C. with a single sequence 46-mer oligonucleotide deduced from peptide #114 (5-CCTCCTGTTCAGCT-CCACAGGCACCCAGAAGTTGATG-GAGACAGG-3') in the same solution containing 100 g/ml of tRNA. Filters were washed in 6 X SSC, 0.1% SDS, 0.05% Pi/PPi at room temperature for 30 minutes and 50° C. for 15 minutes. After overnight autoradiographic exposure, plaques that gave positive signals on duplicate filters were purified by succesive platings and re-screenings. Screening of 5×10⁵ recombinants with the 46-mer yielded eight positive cDNA clones whose sizes ranged from 2.5 to 4.7 kb.

As further confirmation and to select clones containing the most coding sequence, clones were re-screened with the 49-mer and with a 30-mer specified from the p150,95 α subunit N-terminal sequence. Their DNA was purified (Benson, S. A., et al., *Bio Tech.* 4:126–127 (1984)) and their inserts sized and probed with an independent 49-mer derived from peptide 90a (5'-CATCCTGGGTCAGGTCCTGGCCG-CCAGACAGGGCCTGGCCAAAGTACTG-3') and a N-terminus oligonucleotide probe (5'-AGCAGAGT-CCACCCGGAAGGCTGTCAGCTC-3'). Three clones hybridized with the 49-mer and a 4.7 kb clone (λX47) also hybridized with the N-terminal probe and was selected for further study. Additional clones were obtained upon re-screening of the library with fragments from the 4.7 kb cDNA clone.

TABLE 1

PEPTIDE SEQUENCES

| | |
|---|---|
| 60a | Y F T A S L P F E K |
| 60b | X A I G V G(L)A(F)Q N |
| 63a | T T F Q L E L P V K |
| 70 | G A V Y L F H G V L G P S I S P S H S Q |
| 72b | V E D F X A L X(D)I Q N X(L) |
| 79a | X S Y L G Y S T E L A L |
| 90a | L Q Y F G Q A L S G G Q D L T Q D G L V D L A V G A(R) |
| 90b | F G A A L T V L G D V N G D K L T(D)V V |
| 97 | T R P V L W V G V S M Q F I P A E I P(R) |
| 114 | D L P V S I N F(W)V P V E L N Q E A V X M X V E(V) |
| 122 | X S N P L S L L A S V H Q L(Q)G F T Y S A |
| 125a | N F A T M M N F V(R)A V I S Q F Q R P S T Q F |
| 133 | Y K V H N(P S P)X(I) |

EXAMPLE 2

Nucleotide and Deduced Amino Acid Sequence of the p150,95 α cDNA Clone

The λX47 cDNA clone contained an internal Eco RI site. A 670 bp fragment hybridized to the N-terminal probe while a 4.1 kb fragment hybridized to the 46-mer and 49-mer tryptic peptide probes. The Eco RI fragments were subcloned into pUC 18 and pUC 19 and these subclones were used to derive a restriction map (FIG. 2A) using the end-labeling partial digestion procedures of Smith, H. O., et al. (*Nucl. Acid. Res.* 3:2387–2398 (1976)). Fragments were subcloned into M13 mp18 and mp19 (Messing, J., *Met. Enzymol.* 101:20–78 (1978)) and both strands sequenced using the dideoxy nucleotide termination method (Sanger, F., et al., *Proc. Natl. Acad. Sci. USA* 74:5463–5467 (1977)) (FIG. 3). All restriction sites were crossed in both directions. Oligonucleotide primed dideoxy sequencing was used to confirm the sequence of some regions.

The nucleotide sequence of the 4,704 bp insert of λC57 contains a 5' untranslated region of 64 bp, followed by a putative initiation codon and the entire coding sequence of 3492 nucleotides. The 3' untranslated region is 1,140 nucleotides and ends with a consensus polyadenylation signal followed by a stretch of 50 adenosines. An Alu sequence is found between nucleotides 3893 and 4054 in the 3' untranslated region. This region shows 89% homology to the right monomeric unit of the consensus Alu repeat (Deininger P. L, et al., *J. Molec. Biol.* 151:17–33 (1981)). The Alu sequence is preceded by a stretch of 40 thymidines, a common motif corresponding to an inverted Alu sequence polyA-like region. Alu sequences are frequently found in intervening sequences but are uncommon in processed poly(A)+ mRNA (Limborska, S. A., et al., *FEBS Lett.* 212:208–212 (1987)). The presence of the Alu repeat was detected in two other independently isolated cDNA clones, and thus is unlikely to be due to lack of mRNA processing.

The amino acid sequence translated from the cDNA was confirmed by the N-terminal and tryptic peptide sequences. Regions confirmed by amino acid sequencing are underlined in FIG. 3. Of 237 sequenced residues only two discrepancies were found. These were tentative serine assignments which were shown to be threonines by the cDNA sequence.

The p150,95 α subunit N-terminal sequence (Miller, L. J., et al., *J. Immunol.* 137:2891-2900 (1987)) begins at nucleotide 122. Only one potential translation initiation codon is found upstream at position 65. The predicted signal peptide has the expected features including two basic amino acids among the first five residues, predominantly hydrophobic amino acids, and a small amino acid at the cleavage site (von Heijne, G., *J. Molec. Biol.* 173:243-251 (1984)). The mature protein contains 1144 amino acids and the predicted Mr is 125,908, in agreement with previous estimations for the de-glycosylated p150,95 α chain (~132,000 Mr). The putative extracellular domain contains 1081 amino acids with 10 potential N-glycosylation sites. Of these sites, 5 or 6 sites are glycosylated, confirming that this is the extracellular domain and accounting for the rest of the molecular mass. A hydrophobic sequence with features of a transmembrane region separates the extracellular domain from a 30 amino acid hydrophilic cytoplasmic tail. The first two residues of the cytoplasmic domain (Lys—Arg) may act as a stop-transfer signal.

EXAMPLE 3

Tandem Repeats Containing a Putative Divalent Cation-Binding Site

A search for internal homologies in the deduced amino acid sequence revealed the existence of three tandem homologous repeats (I, II, and III) of about 65 residues each located between residues 424 to 619 in the extracellular domain (FIG. 4A). The homology between the repeats is 25% to 33%, significant at $p < 10^{-6}$. The similarity is highest in the central part of the repeats. In the core, 33% of the residues are identical in all three repeats.

The function of the leukocyte adhesion proteins is dependent on divalent cations. The LFA-1-dependent adhesion step in CTL-mediated killing is $Mg^{++}$-dependent. $Ca^{++}$ is insufficient to allow adhesion, but can synergize with low concentration of $Mg^{++}$ (Martz, E., *J. Cell. Biol.* 84:584-598 (1980)), suggesting more than one divalent cation-binding site. A similar $Mg^{++}$ dependence and synergy between $Ca^{++}$ and $Mg^{++}$ is found for LFA-1-mediated homotypic adhesion (Rothlein, R, et al., *J. Exper. Med.* 163:1132-1149 (1986)) and adherence of lymphocytes to artificial membrane bilayers containing the ligand molecule ICAM-1. Furthermore, binding of Mac-1 and p150,95 to the ligand iC3b is divalent cation-dependent (Wright, S.D., et al., *Proc. Natl. Acad. Sci. USA* 80:5699-5703 (1983)); Micklem, K. J., et al., *Biochem. J.* 231:233-236 (1985)).

The 3-dimensional structure of the $Ca^{++}$ and $Mg^{++}$-binding proteins parvalbumin, troponin C and calmodulin has revealed that metal is bound in a turn between two alpha-helices and has defined the amino acid side chains and peptide bond carbonyl oxygens which coordinate the metal (Kretsinger, R. H., et al., *J. Biol. Chem.* 248:3313-3326 (1973)); Herzberg, O., et al., *Nature* 313:653-659 (1985)); Henschen, A., et al., *Ann. N. Y. Acad. Sci.* 408:28-43 (1983)). This metal ion-binding structure has been termed the "EF hand". While some of the divalent cation-binding sites are $Ca^{++}$-specific, others, such as two in troponin C, can bind $Ca^{++}$ or $Mg^{++}$. The central strongly conserved region of the p150,95 α subunit homologous repeats shows striking similarity to these metal-binding sequences (FIG. 5). Oxygen-containing side groups are present at coordination positions +X, +Y, +Z and −X, and there is partial conservation of glycine residues which flank the +Z position. However, the glutamic acid at position −Z is not conserved in p150,95.

EXAMPLE 4

Intervening Sequences Separate the Homologous Repeats

Additional p150,95 α subunit cDNA clones were selected by hybridization with the 4.1 kb Eco RI fragment. Thirty-seven clones were isolated and compared by Sau 3AI digestion and Southern blotting. Most of the clones yielded restriction fragments compatible with the restriction map of the original clone (λX47), but a cDNA clone of 4.4 kb (λX44) showed a distinct pattern. Comparison of the restriction maps of λX47 and λX44 revealed differences 5' to the Pst I site at 1.8 kb (FIG. 2B). Sequencing of this portion of λX44 revealed two regions not found in the original λX47 clone (FIG. 4B). An insert of 120 bp (marked IVS B in FIG. 2B) corresponds in its entire length to an Alu sequence (86% identity to the Alu-clone BLUR 11) (Deininger, P. L., et al., *J. Molec. Biol.* 151:17-33 (1981)). Translation of Alu sequences into protein is very rare (Caras, I. W., et al., *Nature* 325:545-549 (1987)); Sharma, S., et al., *Science* 235:1489-1492 (1987)). Several lines of evidence suggest that the 120 bp insert corresponds to an unspliced intervening sequence. A termination codon in-frame with the preceding coding region is found within this region. Furthermore, consensus donor and acceptor splicing signals flank the insert (5':CAG/agtctc; consensus:CAG/gttgac; 3':ttgcag/C; consensus:ttncag/G) (Mount, 1982). An additional sequence of 230 bp not present in λX47 was detected at the 5' end of λx44 (designated IVS A in FIG. 2B). This sequence is flanked by a potential 3' splice site (ggacag/G). This insert cannot be a coding region since it interrupts tryptic peptide #60b. Therefore, the cDNA clone λX44 appears to be derived from an incompletely spliced p150,95 α subunit mRNA. This result is not surprising since total cellular poly(A)+ mRNA was used for cDNA synthesis.

The 120 bp intron in λX44 separates the homologous repeats II and III (FIG. 4A). This suggests that each of the homologous repeats may be encoded by a different exon, an organization already described for sequences encoding functional units of a protein (Breathnach, R., et al., *Ann. Rev. Biochem.* 50:349-383 (1981)). The other putative intron occurs 155 amino acids before the first homologous repeat. This region may consist of two tandem repeats which show some homology (10% to 21%) to one another and to the other tandem repeats, but this homology is statistically insignificant.

EXAMPLE 5

Homology to the RGD Receptors

The p150,95 α subunit sequence was compared with the complete sequence for the platelet glycoprotein IIb/IIIa α subunit and the partial carboxy terminal sequences of the vitronectin and the fibronectin receptors α subunits (Argraves, W. S., et al., *J. Biol. Chem.* 261:12922-12924 (1986)); Suzuki, S., et al., *Proc. Natl. Acad. Sci.* 83:8614-8618 (1986)) to examine the structural relationships between the leukocyte adhesion protein and RGD (Arg—Gly—Asp) receptor α subunits (FIG. 6). Sequences were aligned with the ALIGN and GENALIGN programs (Intelligenetics). The overall homology between the p150,95 α subunit and the three RGD receptor α subunits was 19% to 20% and was highly statistically significant (p<10$^{-21}$).

The N-terminal 148 amino acids of the p150,95 α subunit are 25% homologous to IIb. The optimal alignment shows that the next region of 126 amino acids present in the p150,95 α chain is absent in IIb. This necessitates the introduction of a gap in the IIb sequence which accounts for most of the difference in length between the p150,95 α subunit (1144 residues) and IIb (1008 residues). A region of 268 residues with 33% homology follows immediately after the gap. This area contains the three putative divalent cation-binding sites of the p150,95 α subunit and three homologous metal ion-binding sites in IIb. The longest region of extensive homology between both chains (residues 431 to 604, 41% identity) corresponds closely to the three tandem putative divalent cation-binding sites. Corresponding EF hand-like motifs in the α subunits of the IIb/IIIa glycoprotein, fibronectin receptor, and vitronectin receptor have also been proposed to bind divalent cations. The conformation of gp IIb/IIIa is dependent on the presence of calcium ions (Kunicki, T. J., et al., *Blood* 58:268–278 (1981)) and IIb binds radioactive calcium (Fujimura, K., et al., *Haemostasis* 50:251a (1983)). The high conservation between p150,95 α and IIb in this region supports the suggestion that the tandem repeats in the p150,95 α subunit are metal ion-binding domains. Furthermore, the high conservation of this region suggests that it may function in ligand binding, as discussed in more detail below. The region containing the putative divalent cation-binding sites is low in cysteine content (1.1%, residues 336–619), as is the preceding region present in p150,95 α but absent in IIb (0%, residues 149–336). The preceding and following regions of the extracellular domain contain 4.1% and 2.6% of cysteine residues, respectively. Of 21 cysteines in the p150,95 α subunit, 15 are conserved in IIb.

In contrast to the p150,95 α subunit, the α subunits of the fibronectin and vitronectin receptors and gp IIb/IIIa consist of two disulfide-bonded chains (heavy and light) which are formed by proteolytic processing of a precursor (Argraves, W. S., et al., *J. Biol. Chem.* 261:12922–12924 (1986)); Suzuki, S., et al., *Proc. Natl. Acad. Sci. USA* 83:8614–8618 (1986)); Charo, I. F., et al., *Proc. Natl. Acad. Sci. USA* 83:8351–8355 (1986)). N-terminal sequencing of the light chains has shown that the proteolytic cleavage (arrowheads in FIG. 6) occurs after a Lys-Arg sequence in the fibronectin and vitronectin receptors and after Ser-Arg in IIb. A Lys-Arg sequence which is a potential additional cleavage site occurs 15 residues towards the N-terminus in IIb/IIIa. The cleavage sites in the three RGD receptor α subunits are located at different positions within a non-homologous stretch of 26 to 35 amino acids. This non-homologous region is deleted in the p150,95 α subunit (gap after residue 998), correlating with the lack of proteolytic processing of the p150,95 α subunit (Springer, T. A., et al., *J. Immunol.* 136:240–245 (1986)); Miller, L. J., et al., *J. Immunol.* 137:2891–2900 (1987)).

A striking region of homology is found in the inner ⅔ of the transmembrane region and includes the two basic stop-transfer amino acids (residues 1096–1116). This string of 21 residues contains 10 positions which are identical in all four α subunits and the overall homology is 62% to 67%. An unusual basic residue within the transmembrane domain is also conserved in all four α subunits. The transmembrane regions of the β subunit of p150,95 and the chicken integrin band III are 70% identical (Kishimoto, T. K., et al., *Cell* 48:681–690 (1987)). The high conservation of both α and β subunit transmembrane sequences suggests that some important interaction may take place in this region, either between the α and β subunits or with other cellular components, possibly involving signal transduction.

EXAMPLE 6

Evolutionary Relationships of Adhesion Receptors

Previous comparisons of the vitronectin receptor, fibronectin receptor and IIb/IIIa α subunit cDNA sequences demonstrate that these RGD receptors are evolutionarily related to each other (Suzuki, S., et al., *Proc. Natl. Acad. Sci. USA* 83:8614–8618 (1986)). The present invention shows that a representative leukocyte adhesion protein α subunit and the RGD-receptor α subunits are extensively related throughout their sequences.

Two subfamilies of RGD receptors have been defined based on their distinct β subunits. These are the fibronectin receptor, integrin, and VLA family with five different α subunits, and the IIb/IIIa and vitronectin receptor subfamily with two different α subunits (Hynes, R. O., et al., *Cell* 48:549–554 (1987)). Together with the leukocyte adhesion receptor subfamily with three α subunits, there are ten distinct α subunits which appear to have evolved from a single primordial gene. Collectively, the three subfamilies have been denoted the integrins (Hynes, R. O., et al., *Cell* 48:549–554 (1987)). N-terminal amino acid sequence homology with the α subunits of the position specific antigens of Drosophila (Leptin, M., et al., *EMBO J.* 6:1037–1043 (1987)) suggests that the evolution of this gene family took place more than 700 million years ago.

The β subunits of the two subfamilies which bind extracellular matrix components are not more related to one another (44%) than to the β subunit of the leukocyte adhesion receptors (37% and 45%). However, comparison of the available α subunit sequences (FIG. 6) reveals that the extracellular matrix receptor α subunits are more similar to one another (27% to 33%) than to the p150,95 α subunit (18% to 20%). Furthermore, the sequence of the Mac-1 α subunit N-terminus (Miller, L. J., et al., *J. Immunol.* (1987)) suggests that the leukocyte adhesion α subunits are more closely related to one another (40% to 50%) than to the α subunits of the other subfamilies.

The extracellular matrix receptors bind to the sequence RGD within their ligands. The close homology suggests that the leukocyte adhesion proteins may also recognize an RGD-like sequence. However, such recognitio sequences must be at least slightly distinct from the hexapeptide containing the RGD sequence in fibronectin, since this peptide does not inhibit LFA-1 dependent adhesion or iC3b receptor function of Mac-1.

EXAMPLE 7

The Ligand Binding Sites of Adhesion Receptors

Figure 7:
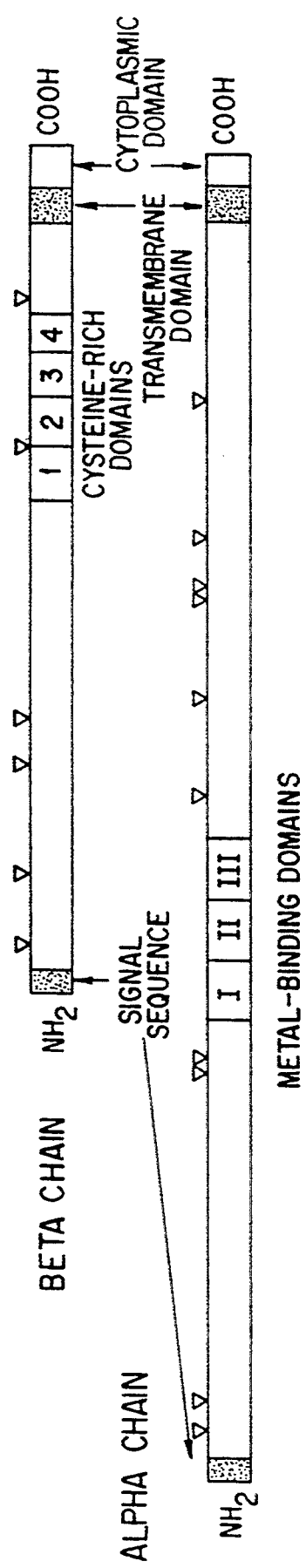
FIG. 7 shows a schematic representation of the complete p150,95 molecule as deduced from the sequencing of cDNA clones. Potential N-glycosylation sites are indicated by triangles.

The overall features of the α and β subunits of the p150,95 molecule, the first nember of the leukocyte adhesion glycoprotein family whose primary structure is completely known, are summarized in FIG. 7. Overall, this structure is very similar to that of the RGD receptors. In additon to the high homology of the β subunits, the four tandem cysteine-rich repeats and all 56 cysteines located throughout the extracellular domain are conserved in all three β subunits (Tamkun, J. W., et al,, *Cell* 46:271–282 (1986)); Kishimoto, T. K., et al., *Cell* 48:681–690 (1987)); Fitzgerald, L. A., et al., *J. Biol. Chem.* 262:3936–3939 (1987)). Divalent cation-binding sites similar to those in the p150,95 α subunit have been found in the α subunits of platelet IIb/IIIa complex, vitronectin receptor (Suzuki, S., et al., *Proc. Natl. Acad. Sci. USA* 83:8614–8618 (1986)), and fibronectin receptor (Argraves, W. S., et al., *J. Biol. Chem.* 261:12922–12924 (1986)). In general, protein families which have such a high degree of homology and similarity in salient structural features have similar tertiary structures and functions. This suggests that these proteins function very similarly in binding ligands, whether the ligands are extracellular matrix proteins, or as in the case of the leukocyte adhesion proteins, cell surface molecules.

The present invention permits several conclusions to be drawn regarding the nature and characteristics of leukocyte cell surface receptors. These conclusions are listed below. The overall features of the α and β subunits of the p150,95 molecule are summarized in FIG. 7.

First, the α subunits of the leukocyte receptors appear to control the ligand specificity. Mac-1 but not LFA-1 binds the ligand iC3b (Sanchez-Madrid, F., et al., *Proc. Natl. Acad. Sci. USA* 79:7489–7493 (1983); Sanchez-Madrid, F., et al., *J. Exper. Med.* 158:1785–1803 (1983)), and although both molecules are present on PMA-differentiated U937 cells, LFA-1 but not Mac-1 mediates homotropic adhesion (Miller, L. J., et al., *J. Immunol.* 137:2891–2900 (1986)). Since Mac-1 and LFA-1 share a common β subunit, the α subunits must control the ligand specificity. Similarly, since the vitronectin receptor and the IIb/IIIa complex share a common β subunit, the different specificities of these receptors must be controlled by the α subunits. These findings strongly suggest that the α subunits contact the ligand, but do not rule out interactions with the β subunits as well. Interaction with the β subunits may be important for maintaining the conformation of the α subunits and the β subunits may be important for maintaining the conformation of the α subunits and the β subunit may also contribute to the ligand binding site (Bennett, J. S., et al., *J. Biol. Chem.* 257:8049–8054 (1982); Gardner, J. M., et al., *Cell* 42:439–448 (1985); Santoro, S. A., et al., *Cell* 48:867–873 (1987)).

Second, a number of the receptors bind multiple, distinct ligands, suggesting the presence of multiple binding sites. The platelet glycoprotein IIb/IIIa binds fibrinogen, fibronectin, vitronectin, von Willebrand factor and probably thrombospondin (Pytela, R., et al., *Science* 231:1559–1562 (1986)). One of the recognition sequences in fibrinogen is different from RGD (Plow, E. F., et al., *J. Biol. Chem.* 259:5386–5391 (1984); Timmons, S., et al., *Proc. Natl. Acad. Sci. USA* 81:4935–4939 (1984)) and evidence suggests that the RGD and non-RGD recognition sequences bind competitively but to distinct areas (Santoro, S. A., et al., *Cell* 48:867–873 (1987)). LFA-1 binds the cell surface molecule ICAM-1, and at least another ligand distinct from ICAM-1 (Rothlein, R., et al., *J. Immunol.* 137:1270–1274 (1986)). Mac-1 and p150,95 bind the ligand iC3b, but also mediate cell-cell adhesion which does not involve iC3b. Mac-1 and p150,95 mediate adhesion of neutrophils and monocytes to endothelial cells and artificial substrates (Springer, T. A., et al., In: Biochemistry of Macrophages (CIBA Symposium 118), Pitman, London, pp. 102–126 (1986)) and p150,95 functions in killer T lymphocyte adhesion to target cells (Keizer, G. D., et al., *J. Immunol.* 138:3130–3136 (1987)). Furthermore, the ability of monoclonal antibodies to distinct epitopes on the Mac-1 α and β subunits to differentially inhibit iC3b binding and cell adhesion suggests distinct binding sites (Anderson, D.C., et al., *J. Immunol.* 137:15–27 (1986); Dana, N., et al., *J. Immunol.* 137:3259 (1987)).

Third, tandem duplication is an evolutionary favored method of generating multiple binding sites. Examples are the low density lipoprotein receptor, containing eight tandem repeats at its N-terminus thought to bind the ligand (Yamamoto, T., et al., *Cell* 39:27–38 (1984)), and Staphylococcus aureus protein A, containing five tandem repeats which bind IgG (Uhlen, M., et al., *J. Biol. Chem.* 259:1695–1702 (1984)).

Fourth, interaction of leukocyte adhesion receptors and extracellular matrix receptors with ligand is dependent on the presence of divalent cations, as discussed above. Divalent cations also influence receptor conformation in the absence of ligand (Kunicki, T. J., et al., *Blood* 58:268–278 (1981)), and thus could indirectly influence the conformation of the ligand binding site. However, the simplest interpretation is that the divalent cations are required because the divalent cation-binding sites and the ligand binding sites are identical or overlapping. Together, these considerations suggest that the tandem, homologous repeats in the α subunit represent multiple binding sites.

Fifth, coordination of the divalent cation with the D (aspartic acid) residue in the ligand sequence RGD contributes to ligand binding. The putative metal binding sites of the p150,95, IIb/IIIa, and vitronectin receptor α subunits are incomplete, since they lack the glutamic acid which is found at the $-Z$ coordinate in clssic $Ca^{++}$ and $Mg^{++}$-binding EF hand loops (FIG. 5 and 6). Instead, hydrophobic residues are found at this position. In clasic metal binding loops, five coordinating residues are in the loop itself, while the glutamic acid forming the $-Z$ coordinate is in the following α helical segment of 9 to 11 residues (Kretsinger, R. H., et al., *J. Biol. Chem.* 248:3313–3326 (1973)). However, in the adhesion receptors, a proline residue is found in a position corresponding to the middle of this helix (arrow in FIG. 4A), showing that this region must have a different, non-α helical structure.

The sequence Gly-Ala-Pro (GAP) is highly conserved in the tandem repeats of both p150,95 and IIb/IIIa α subunits and is also found in the 2 less homologous, more N-terminal repeats in p150,95 and IIb/IIIa (FIG. 6). This suggests that a different backbone structure C-terminal to the residue at the $-X$ coordinate in the adhesion receptors leaves the $-Z$ coordinate of the metal exposed and available for coordination with the aspartic acid in the ligand RGD sequence. The position of the aspartic acid carboxyl group is critical in RGD, because analogues with glutamic acid, only one methylene group larger, or D-aspartic acid, are inactive (Ruoslahti, E., et al., *Cell* 44:517–518 (1986)). In contrast, substitution of D-arginine for L-arginine has little effect.

The glycine residue neighboring the aspartic acid in RGD is of interest, because the presence of glycine residues adjacent to ligating aspartic acids is a feature of metal-binding loops as well (FIG. 5). A fibrinogen peptide has been identified which does not contain RGD but can bind to IIb/IIIa and compete binding of RGD sequences (Santoro, et al., *Cell* 48:867–983 (1987)). This dodecapeptide HHLGGAKQAGDV contains a GD sequence. The conclusion that the divalent cation ligates the D residue in the ligand is therefore consistent with structure/function studies on peptides which bind to adhesion receptors. The unusual conservation of recognition of RGD among at least three different receptors found both in chicken and human (Ruoslahti, E., et al., *Cell* 44:517–518 (1986)); Hynes, R. O., *Cell* 48:549–554 (1987)) further support the conclusion that metal coordinates with the ligand. This is unexpected for protein-protein interactions, since subtle complementary mutations in both the receptor and ligand are likely to change the structure of the receptor site over evolutionary time. Interactions with metal would much more constrain evolution of the ligand structure.

While the invention has been described in connection with specific embodiments thereof, it will be understood that it is capable of further modifications and this application is intended to cover any variations, uses, or adaptations of the invention following, in general, the principles of the invention and including some departures from the present disclosure has come within known or customary practice within the art to which the invention pertains and as may be applied to the essential features hereinbefore set forth and as follows in the scope of the appended claims.

What is claimed is:

1. An isolated nucleic acid molecule comprising a sequence which encodes the α-subunit of human p150,95, wherein said human p150,95 consists of the amino acid sequence depicted in FIG. 3.

2. The nucleic acid molecule of claim 1, wherein said nucleic acid molecule further comprise a vector selected from the group consisting of a plasmid, and a viral vector.

3. The nucleic acid molecule of claim 2, wherein said vector is an expression vector.

4. The nucleic acid molecule of claim 3 wherein said expression vector directs the expression of the alpha subunit of p150,95 in a eukaryotic host.

5. The nucleic acid molecule of claim 2 wherein said expression vector directs the expression of the alpha subunit of p150,95 in a prokaryotic host.

6. The isolated nucleic acid molecule of claim 1 wherein said nucleic acid molecule consists of nucleotide sequence depicted in FIG. 3.

* * * * *